(12) United States Patent
Hadjigeorgiou et al.

(10) Patent No.: US 11,348,479 B2
(45) Date of Patent: May 31, 2022

(54) ACCURACY OF MEASURING NUTRITIONAL RESPONSES IN A NON-CLINICAL SETTING

(71) Applicant: Zoe Limited, London (GB)

(72) Inventors: George Hadjigeorgiou, London (GB); Jonathan Thomas Wolf, London (GB); Richard James Davies, London (GB)

(73) Assignee: Zoe Limited, London (GB)

( * ) Notice: Subject to any disclaimer, the term of this patent is extended or adjusted under 35 U.S.C. 154(b) by 629 days.

(21) Appl. No.: 15/987,699

(22) Filed: May 23, 2018

(65) Prior Publication Data

US 2019/0362648 A1 Nov. 28, 2019

(51) Int. Cl.
| | |
|---|---|
| *G16H 50/20* | (2018.01) |
| *G09B 19/00* | (2006.01) |
| *G06N 20/00* | (2019.01) |
| *A61B 5/00* | (2006.01) |
| *A61B 5/145* | (2006.01) |
| *G06K 7/14* | (2006.01) |
| *G09B 7/00* | (2006.01) |

(Continued)

(52) U.S. Cl.
CPC ........ *G09B 19/0092* (2013.01); *A61B 5/0022* (2013.01); *A61B 5/14532* (2013.01); *A61B 5/4866* (2013.01); *A61B 5/7264* (2013.01); *G06K 7/1413* (2013.01); *G06K 7/1417* (2013.01); *G06N 20/00* (2019.01); *G09B 7/00* (2013.01); *A61B 10/0038* (2013.01); *A63B 24/0062* (2013.01); *A63B 2220/40* (2013.01); *A63B 2230/06* (2013.01)

(58) Field of Classification Search
CPC ...................................................... G16H 50/20

USPC ......................................................... 434/127
See application file for complete search history.

(56) References Cited

U.S. PATENT DOCUMENTS

| | | |
|---|---|---|
| 7,999,674 B2 | 8/2011 | Kamen |
| 8,690,578 B1 | 4/2014 | Nusbaum et al. |
| 9,011,153 B2 | 4/2015 | Bennett et al. |

(Continued)

FOREIGN PATENT DOCUMENTS

| | | |
|---|---|---|
| WO | WO0205702 | 1/2002 |
| WO | WO2008154759 A1 | 12/2008 |

(Continued)

OTHER PUBLICATIONS

Non Final Office Action dated Jan. 10, 2020 for U.S. Appl. No. 15/894,776 "Generating Predicted Values of Biomarkers for Scoring Food" Wolf, 11 pages.

(Continued)

*Primary Examiner* — Kesha Frisby
(74) *Attorney, Agent, or Firm* — Lee & Hayes, P.C.

(57) ABSTRACT

Techniques are disclosed herein for improving the accuracy of nutritional responses measured in a non-clinical setting. Using the technologies described herein, different techniques can be utilized to improve the accuracy of test data associated with one or more "at home" tests. In some examples, more than one test is utilized to improve the accuracy of test data associated with a particular biomarker. In other examples, a data accuracy service can programmatically analyze data received from an individual and determine whether the data is accurate. In some examples, a computing device is utilized to assist in determining what food item(s) are consumed, as well as determine whether a test protocol was followed.

20 Claims, 6 Drawing Sheets

(51) Int. Cl.
*A61B 10/00* (2006.01)
*A63B 24/00* (2006.01)

(56) References Cited

U.S. PATENT DOCUMENTS

| | | |
|---|---|---|
| 2003/0091964 A1 | 5/2003 | Yeager |
| 2009/0275002 A1 | 11/2009 | Hoggle |
| 2011/0091842 A1 | 4/2011 | Dugan |
| 2013/0216982 A1 | 8/2013 | Bennett et al. |
| 2015/0079551 A1 | 3/2015 | Egan |
| 2015/0093725 A1 | 4/2015 | Baarman et al. |
| 2015/0118659 A1 | 4/2015 | Meyer |
| 2015/0140523 A1 | 5/2015 | Dewan |
| 2015/0206450 A1 | 7/2015 | Wayman et al. |
| 2015/0294593 A1 | 10/2015 | Schoen et al. |
| 2015/0294594 A1 | 10/2015 | Pacione et al. |
| 2015/0371553 A1 | 12/2015 | Vento |
| 2016/0035248 A1 | 2/2016 | Gibbs |
| 2016/0042660 A1 | 2/2016 | Radovcic |
| 2016/0049091 A1 | 2/2016 | Omidi |
| 2016/0049092 A1 | 2/2016 | Barnett et al. |
| 2016/0063888 A1 | 3/2016 | McCallum et al. |
| 2016/0071423 A1 | 3/2016 | Sales et al. |
| 2016/0071432 A1 | 3/2016 | Kurowski et al. |
| 2016/0098942 A1 | 4/2016 | Messier |
| 2016/0140869 A1 | 5/2016 | Kuwahara et al. |
| 2016/0166195 A1 | 6/2016 | Radecka et al. |
| 2016/0232311 A1 | 8/2016 | Segal et al. |
| 2016/0253922 A1 | 9/2016 | Kremen et al. |
| 2016/0379520 A1 | 12/2016 | Borel et al. |
| 2019/0362848 A1 | 11/2019 | Wolf et al. |
| 2020/0065681 A1 | 2/2020 | Wolf et al. |
| 2020/0066181 A1 | 2/2020 | Hadjigeorgiou et al. |

FOREIGN PATENT DOCUMENTS

| | | |
|---|---|---|
| WO | WO2015166489 | 11/2015 |
| WO | WO2018031991 | 2/2018 |

OTHER PUBLICATIONS

Non Final Office Action dated Jan. 10, 2020 for U.S. Appl. No. 15/894,798 "Generating Personalized Nutritional Recommendations Using Predicted Values of Biomarkers" Wolf, 12 pages.

Final Office Action dated Jul. 10, 2020 for U.S. Appl. No. 15/894,776, "Generating Predicted Values of Biomarkers for Scoring Food", Wolf, 6 pages.

Final Office Action dated Jul. 10, 2020 for U.S. Appl. No. 15/894,798, "Generating Personalized Nutritional Recommendations Using Predicted Values of Biomarkers", Wolf, 6 pages.

PCT Search Report dated May 21, 2019, for PCT Application No. PCT/IB2019/051088, 11 pages.

PCT Search Report dated May 21, 2019, for PCT Application No. PCT/IB2019/051089, 12 pages.

Anonymous, "Glucose meter—Wikipedia", retrieved on Oct. 30, 2019 at <<https://en.wikipedia.org/w/ index php?Title=Glucosemeter &oldid=851737873#Noninvasive_meters>>, Jul. 24, 2018, 15 pages.

Carson et al, "Challenges for measurement science and measurement practice: the collection and interpretation of home-monitored blood glucose data", Measurement, vol. 24, No. 4, Institute of Measurement and Control, Dec. 1, 1998, pp. 281-293.

Edelman et al, "Multisite Evaluation of a New Diabetes Self-Test for Glucose and Glycated Protein (Fructosamine)", Diabetis Technology & Therapeutics, vol. 2, No. 2, Jan. 1, 200, pp. 233-238.

Kulkarni, "Comparision of Image Recognition APIs on Food Images", retrieved on Oct. 19, 2019 at <<https://byles.grubhub.com/https-medium-com-rohan-kulkarni comparison-of-image-recognition-apis-on-food-images-cddc9105fc33>>, pp. 1-9.

PCT Search Report and Written Opinion dated Nov. 22, 2019 for PCT Application No. PCT/EP2019/072806, 15 pages.

PCT Search Report and Written Opinion dated Nov. 8, 2019 for PCT Application No. PCT/EP2019/071801, 14 pages.

PCT Search Report and Written Opinion dated Dec. 5, 2019 for PCT Application No. PCT/EP2019/072804, 14 pages.

Seeberg et al, "Development of a weable multisensor device enabling continuous monitoring of vital signs and activity", IEEE-EMBS International Conference on Biomedical and Health Informatics (BHI), IEEE, Jun. 1, 2014, pp. 213-218.

Tushuizen et al, "Postprandial lipid and apolipoprotein responses following three consecutive meals associate with liver fat content in type 2 diabetes and the metabolic syndrome", Atherosclerosis, vol. 211, No. 1, Elsevier, Amsterdam, NL, Feb. 10, 2010, pp. 308-314.

Von Niederhausem et al, "Validity of mobile electronic data capture in clinical studies: a pilot study in pediatric population", BMC Medical Research Methodology, vol. 17, No. 1, Dec. 1, 2017, 10 pages.

Wolcott et al, "Laboratory Medicine: A National Status Report Division of Laboratory Systems National Center for Preparedness, Detection, and Control of Infectious Diseases Centers for Disease Control and Prevention—The Lewin Group under Subcontract to Battelle Memorial Institute", retrieved on Nov. 25, 2019 at <<http://www.lewin.com/content/dam/Lewin/Resources/Site_Sections/Publications/39931»>, May 1, 2008, 385 pages.

Yun et al, "Smartphone-based point-of-care lipid blood test performance evaluation compared with a clinical diagnostic laboratory method", arxiv.org, Cornell University Library, Ithaca, NY, Apr. 19, 2018, 8 pages.

PCT Search Report dated Sep. 3, 2019, for PCT Application No. PCT/EP2019/063330, 15 pages.

Office Action for U.S. Appl. No. 16/120,039, dated Mar. 22, 2021, Hadjigeorgiou, "Generating Personalized Food Recommendations from Different Food Sources", 12 pages.

International Preliminary Report on Patentability dated Mar. 11, 2021 for PCT Application No. PCT/EP2019/072804, 9 pages.

Non Final Office Action dated Oct. 7, 2020 for U.S. Appl. No. 16/434,135, "Using at Home Measures to Predict Clinical State and Improving the Accuracy of At Home Measurements/Predictions Data Associated with Circadian Rhythm and Meal Timing", Wolf, 6 papges.

Non Final Office Action dated Jul. 9, 2021 for U.S. Appl. No. 16/434,135, "Using at Home Measures to Predict Clinical State and Improving the Accuracy of At Home Measurements/Predictions Data Associated with Circadian Rhythm and Meal Timing", Wolf, 6 pages.

ACCURACY OF MEASURING NUTRITIONAL RESPONSES IN A NON-CLINICAL SETTING

BACKGROUND

Today, individuals have a large variety of food choices. Determining healthy food choices for an individual can be challenging. Complicating the selection of food that is healthy for an individual are factors that are personal to the user. Age, sex, weight, the microbiome, as well as other characteristics of an individual affect what foods an individual should select to eat. In some cases, what foods to eat may be selected based on how particular foods affects the biomarkers of an individual such as glucose, triglycerides and insulin. For example, the glucose of an individual may be measured before and after eating a specified food(s). These measurements may be taken during free living, or in a clinical setting. Free living measurements, such as those taken at home or at work, are often cheaper, however they can be less accurate than measurements taken in a clinical setting, such as in a hospital or a lab. The accuracy and reliability of the measurements can affect what foods are recommended for an individual.

DETAILED DESCRIPTION

Figure 1:
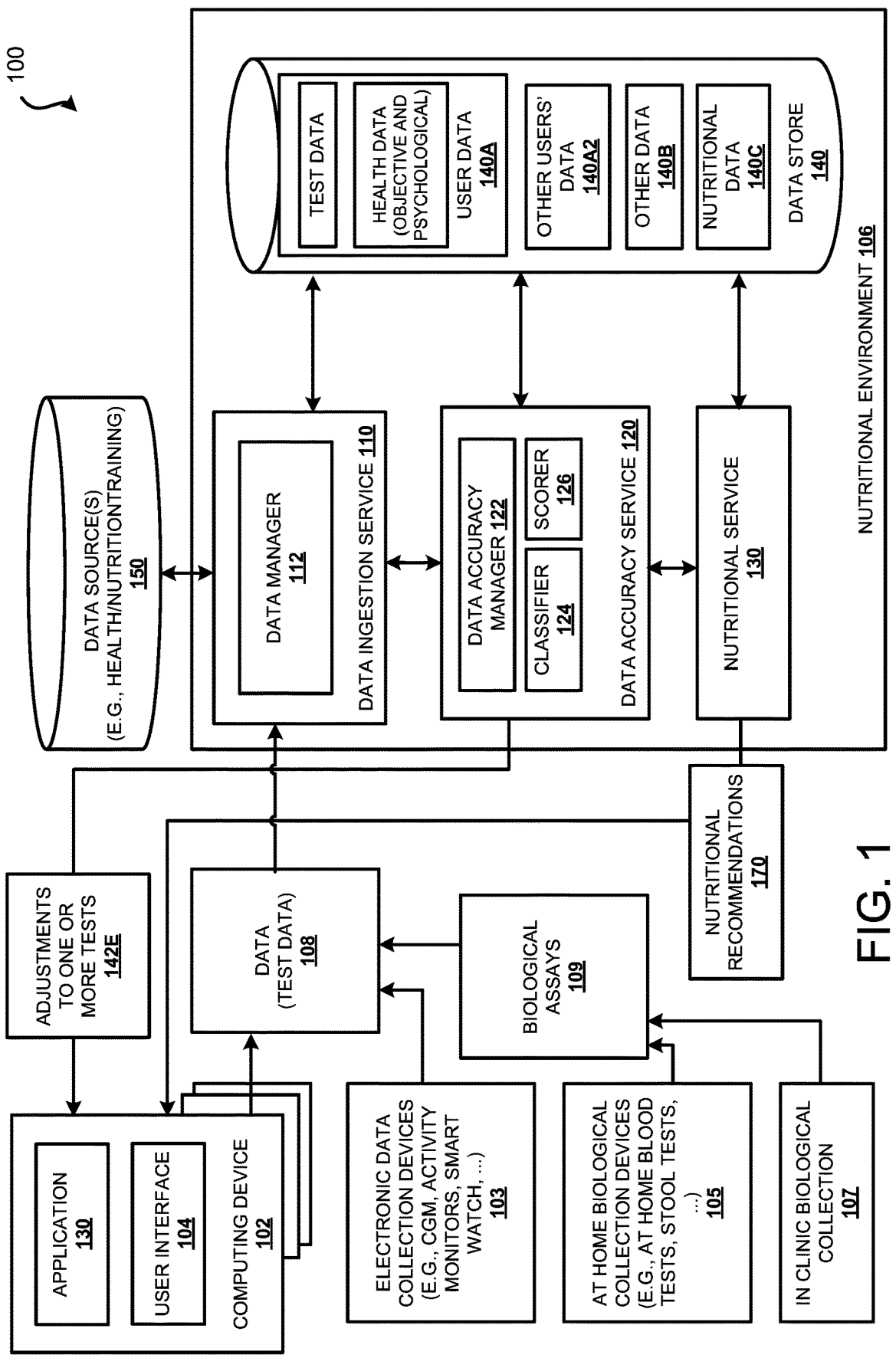
FIG. 1 is a block diagram depicting an illustrative operating environment in which test data associated with at home measurements of nutritional responses is analyzed to address any inaccurate test data detected.

The following detailed description is directed to technologies for improving the accuracy of measuring nutritional responses in a non-clinical setting. Using the technologies described herein, the measurement and accuracy of nutritional responses recorded outside of a clinical setting may be improved. For example, the measurement of nutritional responses for one or more biomarkers at home can be improved using the technologies described herein.

Nutritional responses to food vary between individuals. To understand these differences, dynamic changes in biomarkers caused by eating food such as a standardized meal ("post-prandial responses") are measured. By understanding a particular individual's nutritional responses, in terms of blood biomarkers such as glucose, insulin and triglycerides levels, or non-blood biomarkers such as the microbiome, a nutritional service may be able to choose the food that is more suited for that particular person.

While clinical facilities are able to provide accurate post-prandial data, not only can the cost be prohibitive, the number of individuals agreeing to go to clinical facilities is limited. Bringing individuals into a clinical facility for multiple days to measure responses to different food is very expensive. If at home measurement can be made sufficiently accurate, then much larger volumes of nutritional response data can be collected than has been possible historically.

Measuring post-prandial responses primarily outside of a clinical facility ("at home") can result in data that is not as accurate as desired. Clinical facilities typically generate accurate data and have therefore, historically, been utilized to obtain data associated with post-prandial responses. Generally, clinical facilities are able to generate accurate data amongst other reasons because (1) experiments are performed in controlled conditions to minimize contamination and maximize user compliance, (2) trained medical staff extract venous blood or collect other biological materials, (3) the biological samples can be treated to minimize inaccuracy by for example collecting in specially prepared tubes containing the right chemicals, centrifuging blood within the required time, and/or freezing samples at −80 degrees centigrade once extracted to prevent any changes to the sample, (4) sending the materials often still frozen to be measured with the highest quality assays. At home tests, in contrast, do not appear to use these techniques. Using the techniques described herein, the accuracy of the at home tests can be improved over traditionally obtained at home measurements. This allows large numbers of people to provide useful nutritional data at a lower cost than previously possible.

A "biomarker" or biological marker generally refers to a measurable indicator of some biological state or condition associated with an individual. Stated another way, a biomarker may be anything that can be used as an indicator of particular disease, state or some other physiological state of an organism. A biomarker can typically be measured accurately (either objectively and/or subjectively) and the measurement is reproducible (e.g., blood glucose, triglycerides, insulin, c-peptides, ketone body ratios, IL-6 inflammation markers, hunger, fullness, and the like). The measured biomarkers can include many different types of health data such as microbiome data, blood data, glucose data, ketone data, nutrition data, wearable data, genetic data, biometric data, questionnaire data, psychological data (e.g., hunger, sleep quality, mood, . . . ), objective health data (e.g., age, sex, height, weight, medical history, . . . ), as well as other types of data. Generally, "health data" can refer to any psychological, subjective and/or objective data that relates to and is associated with one or more individuals. The health data might be obtained through testing, self-reporting, and the like. Some biomarkers change in response to eating food, such as blood glucose, insulin, c-peptides and triglycerides.

In some examples, the data includes "wearable" test data obtained from electronic data collection devices worn and/or utilized by an individual. For instance, an individual may wear a fitness device, such as an activity-monitoring device, that monitors motion, heart rate, determines how much an individual has slept, the number of calories burned, activities performed, blood pressure, body temperature, and the like. The individual may also wear a continuous glucose meter (CGM) that monitors blood glucose levels often by measuring levels of glucose in interstitial fluid.

An individual may also provide test data obtained using a variety of devices, such as but not limited to blood glucose monitors including CGMs, "At Home Blood Tests" which use blood extraction devices such as finger pricks which in some examples are used with dried blood spot cards, wearable activity trackers, blood pressure monitors, and the like. In some examples there may be home biological collection devices such as a stool test which collect a biological sample which is then assayed to produce test data. An individual may also input test data into one or more software applications (or provide the data some other way) that can be utilized. For example, an individual may enter the food they consumed for a particular test, a value indicated by a measurement device, and the like.

In some examples, the user may scan a barcode or QR code that is associated with food to generate test data that can identify the food. In other examples, the user may take one or more digital pictures of the food to generate test data that can identify the food. In some examples the captured images can be programmatically analyzed to identify the type of food as well as the quantity of food. As another example, an individual may input test data determined from one or more tests, such as urinalysis test strips, blood test strips, and the like. The test data may come from different sources, such as but not limited to from one or more of an individual, a lab, a doctor, an organization, and/or some other data source.

According to some examples, two or more measurements of one or more biomarkers are combined to increase the accuracy of the measurement of nutritional responses. For instance, combining at home CGM and at home blood measurements may be used to more accurately measure the response of multiple biomarkers to the nutritional input, since the input must be the same for both measurements. In other examples measuring fasting bloods on more than one occasion and combining this data can be used to more accurately measure nutritional responses for one or more biomarkers.

A computing device, such as a mobile phone or a tablet computing device can also be used to improve the accuracy of the measurements. Instead of relying on an individual accurately recording the time a test was taken, or a food was eaten, the computing device can record information that is associated with the event. For instance, the computing device may be utilized to obtain timing data associated with the timing of the test (e.g., the time the food was consumed, the measurement(s) taken, . . . ). As an example, a clock (or some other timing device) of the computing device may be used to record the time the food was consumed and/or when the measurement(s) were collected. In other instances, a camera of the computing device can be used to capture photographic data such as digital photographs associated with the measurements. In other examples, the computing device can be used by an individual to scan a barcode of a food before they eat that food. The barcode can be used to correctly identify the food as well as the portion size of the food. In other examples, an individual (or some other device within an environment of the user) can capture one or more images of the food eaten. In other examples, some other identification technique, such as Near Field Communication (NFC), can be utilized to identify the food. This timing data, photographic data and other data may be considered non-biomarker test data. As briefly discussed above, the image(s) can be programmatically analyzed to automatically identify the food within the image as well as the quantity of the food.

The images might be taken before and after eating food such that a comparison can be made as to how much food was actually eaten. In addition to identifying the food, the computing device can be used to identify other data about the event, such as the time of the event. The computing device might also be used to capture an image of a test performed by the user. For instance, the user can take a picture of a blood spot on a card. This image can then be programmatically or manually analyzed to determine that the captured blood spot meets one or more criteria (e.g., fills the spot, does not overfill the spot, . . . ). In other examples, an individual might scan a barcode or QR code of a test device, such as a blood spot card. The scan can be used to correctly identify which test device was used for which test. This can be applied to other at home biological collection devices, including blood tests and stool tests.

Alternatively, and/or in addition to the above, other measurements can be taken to assist in determining when a particular food was eaten and/or a test was performed. For example, in some cases a CGM can be used to confirm the start point of a meal used for at home blood measurement. In this example, for some meals data recorded by an individual about when they started to eat can be verified by changes in glucose detected by the CGM.

In other examples, insulin post-prandial responses can be calculated by modelling insulin levels via c-peptide levels from at home blood measurements. C-peptide is released into the blood as a byproduct of the formation of insulin by the pancreas. A c-peptide test measures the amount of c-peptide in a blood or urine sample. Post-prandial c-peptide response can be used to provide an estimate of the insulin response. According to some examples, the accuracy of the at home measurements can be enhanced by lab/clinical measurements on the same user or other users using some combination of the same at home testing method and/or higher accuracy clinical assays.

Instead of eating a single meal one time and recording the nutritional response once, the test may be repeated one or more additional times to improve the accuracy of the at home testing. The repeating of the eating of the same food can be used to obtain more accurate blood measurements of nutritional responses as compared to eating a single meal of the food.

According to some examples, at home meals/food consumed by the individual can consist of different nutritional compositions (e.g., carbohydrates/protein/fat . . . ). Varying the at home meals assists in obtaining a large range of nutritional responses.

Data from a variety of sources can be used by a data accuracy service, or some other service, in determining the accuracy of test data associated with at home tests. For instance, data can be utilized from questionnaires, camera, phone based food logging, CGM, support team, and/or activity monitoring to improve accuracy by cross-checks, and the like. For instance, data from a CGM may indicate a glucose spike even though there is not a corresponding entry of a logged food, a photo might not match a food description, food logging might not match self-reported eating habits from a questionnaire, the user may be logging too little food to cover their calorie requirements calculated from a questionnaire, data from a CGM may indicate a glucose spike too big for the food that was logged, and the like. In yet other examples, the computing device can store an offline food database such that data can be accessed even when an individual is not connected to the Internet and/or some other network. In some examples, the data accuracy service 120 utilizes a machine learning mechanism to assist in determining the accuracy of the test data.

Additional details regarding the various components and processes described above relating to improving the accuracy of measuring nutritional responses in a non-clinical setting will be presented below with regard to FIGS. 1-6.

It should be appreciated that the subject matter presented herein may be implemented as a computer process, a computer-controlled apparatus, a computing system, or an article of manufacture, such as a computer-readable storage medium. While the subject matter described herein is presented in the general context of program modules that execute on one or more computing devices, those skilled in the art will recognize that other implementations may be performed in combination with other types of program modules. Generally, program modules include routines, programs, components, data structures and other types of structures that perform particular tasks or implement particular abstract data types.

Those skilled in the art will also appreciate that aspects of the subject matter described herein may be practiced on or in conjunction with other computer system configurations beyond those described herein, including multiprocessor systems, microprocessor-based or programmable consumer electronics, minicomputers, mainframe computers, handheld computers, personal digital assistants, e-readers, mobile telephone devices, tablet computing devices, special-purposed hardware devices, network appliances and the like.

In the following detailed description, references are made to the accompanying drawings that form a part hereof, and that show, by way of illustration, specific examples or examples. The drawings herein are not drawn to scale. Like numerals represent like elements throughout the several figures (which may be referred to herein as a "FIG." or "FIGS.").

FIG. 1 is a block diagram depicting an illustrative operating environment 100 in which test data associated with at home measurements of nutritional responses is analyzed to address any inaccurate test data detected. An individual, such as an individual interested in obtaining personal nutritional recommendations 170, may communicate with the nutritional environment 106 using a computing device 102. In some configurations, one or more electronic data collection devices 103 can be used to collect test data 108. For example, the electronic collection devices can be configured as a CGM, an activity monitor, a smart watch, and the like. Some of this test data may be biomarker test data, such as blood glucose results collected by the CGM. Some of this test data may be non-biomarker test data such as photos and time stamps.

In some configurations, test data can be obtained using one or more at home biological collections devices such as At Home Blood Tests or a stool test to produce a biological sample. The samples can be delivered to a lab where the sample is assayed by one or more biological assays 109 which produce biomarker test data which is added to the test data 108. In some configurations, the user is a customer of the nutritional environment 106 and the computing device 102 is a mobile computing device (e.g., a mobile phone).

As illustrated in FIG. 1, the operating environment 100 includes one or more computing devices 102 in communication with a nutritional environment 106. In some examples, the nutritional environment 106 may be associated with and/or implemented by resources provided by a service provider network such as provided by a cloud computing company. The nutritional environment 106 includes a data ingestion service 110, a data accuracy service 120, a nutritional service 130, and a data store 140. The nutritional service 130 can be utilized to generate personalized nutritional recommendations 170. For example, the personalized nutritional recommendations can be generated using techniques described in U.S. patent application Ser. No. 15/894,798, filed on Feb. 12, 2018, which is incorporated by reference herein in its entirety.

The nutritional environment 106 may include a collection of computing resources (e.g., computing devices such as servers). The computing resources may include a number of computing, networking and storage devices in communication with one another. In some examples, the computing resources may correspond to physical computing devices and/or virtual computing devices implemented by one or more physical computing devices.

It should be appreciated that the nutritional environment 106 may be implemented using fewer or more components than are illustrated in FIG. 1. For example, all or a portion of the components illustrated in the nutritional environment 106 may be provided by a service provider network (not shown). In addition, the nutritional environment 106 could include various Web services and/or peer-to-peer network configurations. Thus, the depiction of the nutritional environment 106 in FIG. 1 should be taken as illustrative and not limiting to the present disclosure.

The data ingestion service 110 facilitates submission of data utilized by the data accuracy service 120 and, in some configurations, the nutritional service 130. Accordingly, utilizing a computing device 102, an electronic collection device 103, an at home biological collection device 105 or via in clinic biological collection 107, an individual may submit data 108, such as test data, to the nutritional environment 106 via the data ingestion service 110. Some of the test data 108 may be biomarker test data, and some of the test data 108 may be non-biomarker test data such as photos, barcode scans or timing data. The data may also be obtained by the data ingestion service 110 from other data sources, such as data source(s) 150. For example, the data source(s) 150 can include, but are not limited to nutritional data (e.g., nutrition of particular foods, nutrition associated with the individual, and the like), health data records associated with the individual and/or other individuals, and the like.

The data, such as data 108, or the data obtained from one or more data sources 150, may then be processed by the data manager 112 and/or the data accuracy manager 122 and included in a memory, such as the data store 140. As illustrated, the data store 140 can be configured to store user data 140A, other users' data 140A2, other data 140B, and nutritional data 140C (See FIG. 2 for more details on the data ingestion service 110). In some examples, the user data 140A and other users' data 140A2 includes test data and health data that can include psychological data, subjective health data and objective health data. According to some examples, the test data is associated with at home measurements of nutritional responses to food. In some examples, data sources 150 may include training data that can be obtained from a number of individuals (e.g., >100, 500, 1000, . . . ). This training data may be the results of at home and clinical measurements of nutritional responses using the same or different devices as used for the test data 108. This training data can be utilized by a machine learning mechanism or other automated program to determine the level of accuracy of the test data 108 associated with an at home measurement of a nutritional response. Some of the individuals in the training data may have been subject to similar tests and procedures as used to generate the test data. Some of the individuals in the training data may have generated data in a clinical setting using both at home measurements and high accuracy clinical measurements at the same time, so as to provide an accurate measure for a biomarker alongside the result generated by the at home measurement process.

As discussed in more detail below, the data accuracy service 120 utilizing the data accuracy manager 122 can determine the level of accuracy of data 108 associated with an at home measurement of a nutritional response. As briefly discussed above, the at home measurements are associated with at least two different at home sources of data (e.g., combining at home CGM and at home blood measurements, or combining time recorded on a computing device with blood measurements). The data accuracy service 120 can be configured to generate a value indicating an accuracy of the test data. In some examples, the data accuracy service 120 utilizes data associated with the user providing the data in addition to data from other users performing similar tests. In other examples, the data utilized is associated only with the user. According to some examples, the data can include test data obtained from a clinical setting, which is typically more accurate than at home measurements. For instance, the data accuracy manager 122 may compare test data for fasting biomarkers measured at home with test data for fasting biomarkers measured at a clinical setting. According to some examples, it may use data to ascertain the accuracy of a particular data collection device and weight the data from that device accordingly compared to other devices. According to some examples, the data accuracy service 120 is configured to determine the level of accuracy of test data for the biomarkers associated with insulin, glucose, c-peptide, ketone bodies, triglycerides, IL-6 inflammation, microbiome, hunger, fullness, mood, and the like for an individual.

In some examples, the data accuracy manager 122 may utilize one or more machine learning mechanisms. For example, the data accuracy manager 122 can use a classifier 124 to classify the accuracy of test data within a classification category. In other examples, the accuracy manager 122 may use a scorer 126 to generate a score that provides an indication of the likely level of accuracy of the test data for a biomarker.

The data ingestion service 110 and/or the data accuracy service 120 can generate one or more user interfaces, such as a user interface 104, through which an individual, utilizing the computing device 102, or some other computing device, may provide/receive data from the nutritional environment 106. For example, the data ingestion service 110 may provide a user interface that allows an individual of the computing device 102 to submit test data to the nutritional environment 106. The data accuracy service 120 may provide a user interface 104 that provides adjustments and/or instructions to the user for performing at home tests for nutritional responses.

As briefly mentioned above, instead of using a single at home test to measure a single biomarker (e.g., a blood glucose response) to a meal, more than one test to measure the single biomarker (or another biomarker that is correlated to the single biomarker) may be utilized. By combining these results, data accuracy service 120 can improve the level of accuracy of the calculated nutritional response. In some examples, the data accuracy service 120 determines accuracy of at home measurements for one or more of insulin, c-peptide, glucose, ketone bodies, IL-6 inflammation and triglycerides. Insulin, glucose and triglycerides are components that can affect body weight.

In some cases, the individual can also provide biological samples to a lab for testing, using a biological collection device 105. According to some configuration this will include At Home Blood Tests. According to some configurations, individuals can provide a sample for microbiome analysis. As an example, metagenomic testing can be performed using the sample to allow the DNA of the microbes in the microbiome of an individual to be digitalized. Generally, a microbiome analysis includes determining the composition and function of a community of microbes in a particular location, such as within the gut of an individual. An individual's microbiome appears to have a strong causal relationship to metabolism, weight and health, yet only ten to thirty percent of the microbiome is common across different individuals. Instead of performing a single test for determining a nutritional response, techniques described herein combine different techniques to assist in improving the accuracy of the data captured outside of a clinical setting.

According to some configurations, individuals can provide a sample or samples of their stool for microbiome analysis as part of the at home biological collection, 105. In some cases, this sample may be collected without using a chemical buffer. The sample can then be used to culture live microbes, or for chemical analysis such as for metabolites or for genetic related analysis such as metagenomic or meta-transcriptomic sequencing. In such cases it may suffer from changes in microbial composition due to causes including microbial blooming from oxygen in the period between being collected and when it is received in the lab, where it will be immediately assayed or frozen. In some cases, to avoid this change in bacterial composition after collection, the sample may be frozen at low temperatures such as minus 80 degrees centigrade very rapidly after collection. The sample can then be used to culture live bacteria, or for chemical analysis or for metagenomic sequencing. This collection can be done as part of an in clinic biological collection or at home where the collection kit is configured to deliver such low temperatures, and maintain them until a courier has taken the sample to a lab.

A stool sample may be combined with a chemical preservation buffer such as ethanol as part of the at home collection process to stop further microbial activity, which allows a sample to be kept at room temperature before being received at the lab where the assay is done. This buffer allows for such a sample to be posted in the mail without issues of microbial blooming or other continuing changes in microbial composition. The buffer may however prevent some biochemical analyses from being done, and because preservation buffers are likely to kill a large fraction of the microbial population it is unlikely that samples conserved in preservation buffers can be used for cultivation assays.

In some cases, a user may do multiple stool tests over time, so that one can measure changes in the microbiome over time, or measure changes in the microbiome in response to meals, or changes in the microbiome in response to other clinical or lifestyle variations.

In some examples, the stool sample may be collected using a scoop or swab from a stool that is collected by the user using a stool collection kit that prevents the stool from falling into a toilet. Because there is a very high microbial load in the gut microbiome compared, for example, to the skin microbiome it is also possible that in some cases the stool sample is taken from paper that is used to clean the user's behind after they have passed a stool. This is only possible if the quantity of stool is large enough that the microbes from the stool greatly exceed the microbes that will be picked up from the user's skin or environmental contaminants. In any of these cases the scoop, swab or tissue may be placed inside a vial that contains a buffer solution. If the user then ensures the stool comes into contact with the buffer for example by shaking then this stops further microbial activity and allows the solution to be kept at room temperature without a significant change in microbial composition. In some cases, a sterile synthetic tissue can be used that does not have biological origins such as paper, so that when the DNA of the sample is extracted there is no contamination from the tissue. According to some examples, the tissue can be impregnated with a liquid to help capture more stool from the user's skin, where the liquid does not interfere with the results of the stool test and is not potentially dangerous for the human body.

In some cases, the timing and quality of the stool sample can be recorded using the computer device, 102, for example using a camera. Where there are multiple stool tests the computer device 120 can use a barcode (or some other identifier) to confirm the timing and identity of that particular sample.

While the data ingestion service 110, the data accuracy service 120, the nutrition service 130 are illustrated separately, all or a portion of these services may be located in other locations or together with other components. For example, the data ingestion service 110 may be located within the data accuracy service 120. Similarly, the accuracy manager 122 may be part of a different service, and the like.

At home measurements for different biomarkers can be obtained over some period of time. In some examples, the period individuals may perform at home measurements may range from one day to a few weeks. In other examples, the period ranges over some other duration. Generally, the longer the period the measurements are taken results in higher cost and more information gathered. There can also be a greater risk of non-compliance by the user as the duration of the measurements is lengthened. In other examples, there are multiple periods of measurement. For example, measurements may be taken at different points in time (e.g., every other day, once a week, every six months, over two weeks with a separate clinical visit a month later, . . . ). In some cases, the measurements are taken by electronic data collection devices 103, such as the Continuous Glucose Monitor (CGM), that have a limited operating duration. As discussed above, test data 108 can also come from other sources, such as at home biological collection devices 105, and/or in-clinic biological collection.

In order to assist in obtaining accurate measurements, the computing device 102, may be a mobile computing device (e.g., a mobile phone or tablet) that can be utilized to assist in improving the accuracy of the at home measurements of the nutritional responses. For example, an application 130 executing on the mobile phone, or at some other location, can be utilized to record different information associated with the at home measurements. The information captured by the computing device can include a variety of information, such as time of day, temperature, one or more pictures, textual input, voice input, barcode scans, QR code scans, and the like.

In some examples, the application 130 can be configured to operate without connectivity to the Internet. For example, the individual can take measurements and utilize the application to record information associated with the measurements, without Internet connectivity. When connectivity is restored, the application 130 can connect to the Internet to provide authorized information to one or more other computing devices. According to these configurations, the computing device may store at least the portion of a nutritional database that the user accesses to record food, in order to help ensure that data can still be captured by the application without Internet connectivity. In some examples, the information is provided to the one or more computing devices of the nutritional environment. The data accuracy service 120 can then analyze the information programmatically and/or manually and determine information and accuracy about the measurements being performed.

To provide a more complete understanding of determining nutritional responses to a particular food, an example protocol will now be described. It will be appreciated that changes can be made to the following steps and procedures.

In some examples, food item(s) selected for a particular test are standardized across different individuals. These "standardized meals" are carefully measured meals that can be packaged and eaten by the individual at home. Instructions are provided to the users to eat the meal at predefined times (e.g., after waking up without eating anything else.). In some examples, more than one meal is utilized. As will be discussed in more detail below, meals that include different nutritional ratios may be included. The at home tests performed can include one or more blood tests that are taken at different points in time relative to when the meal is consumed, depending on biomarkers being measured.

If only a single meal is to be eaten, the components of carbohydrate, fat, protein ("macronutrients") and fiber are chosen to help ensure that on average there is a significant post-prandial change in the individual's target biomarkers. For example, if the target is to measure blood glucose and blood lipids, the meal will have significant carbohydrate levels (e.g. above 30 grams) and fat levels (e.g. above 20 grams.) If there are a series of standardized meals, the standardized meals can be chosen to expose the individual to a range of levels of macronutrients so as to measure the interpersonal variability of biomarker responses. One example series of meal might be: (1) metabolic challenge (50 g fat, 85 g Carbohydrate); (2) high fat breakfast (35 g fat, 35 g Carbohydrate); (3) medium fat breakfast (22 g fat, 71 g carbohydrate), (4) low fat/high carbohydrate breakfast (9 g fat, 95 g Carbohydrate); (5) Oral Glucose Tolerance Test. (0 g fat, 75 g Carbohydrate). Other series of meals can be utilized.

Nutritional responses to these meals can be measured using one or more tests. In some examples, at home blood tests can be utilized to not only identify the post-prandial response to these individual meals, but may also be utilized to predict responses to meals that were not measured by for example building a model linking biomarker responses to the quantities of macronutrients. This model can be implemented within a nutritional service 130 as described herein.

These standardized meals can be designed to avoid some of the complexities of the food matrix, bioaccessibility and bioavailability. The complexities of the food matrix, bioaccessibility and bioavailability refer to fact that the amount of nutrients absorbed by the body are not the same as are measured in the lab for the food. As an example, the body extracts only about a third of the calories in whole almonds, but almost all of the calories in ground almonds. The standardized meals can also be designed to minimize the impact of non-nutritive bioactives which change the metabolism of the individual (e.g. polyphenols). Even simple products like wholemeal bread and cheese are in fact highly complex, leading to a risk of variability between apparently identical meals and a complex interplay of factors beyond the macronutrients in the meal. The standardized meals are designed to try and keep factors other than the target nutrients constant (e.g. keeping levels of fiber and protein constant if only changes in fat and carbohydrate are to be measured). It is also possible to design a series of standardized meals to explore nutrients other than macronutrients (e.g. by changing the fiber in the meal but keeping the other components constant).

One approach to providing standardized meals is to make muffins, using plain flour, baking powder, egg white, caster sugar, skimmed milk and oil. If the meals are muffins, many days worth of food can be provided to the individual at one time as a muffin can be frozen and defrosted without significant changes to the food matrix and/or nutritional composition, unlike certain products such as bread.

The percentage of carbohydrate, fat and protein can be manipulated easily with such an approach while ensuring that the meal structure is the same. The oil utilized is standardized. There are multiple options including an oil that is representative of the average oil used in that country (for example with representative proportions of different SFA's such as myristic, palmitic, stearic as well as Unsaturated Fatty Acids (UFA) (UFAs's oleic, linoleic and alpha-linolenic) or a single oil such as high oleic sunflower oil ("HOS"). HOS, with around 80% oleic acid, is generally preferable as it elicits what could be described as an 100% lipaemic response. Other fats elicit variable lipaemic responses due to differences in solid fat content, TAG sn-2 positional composition and presence of medium chain fatty acids. Therefore, to distinguish difference between fats, HOS gives a clean 'reference response'.

In some examples, at least a portion of the standardized meals are consumed for the first meal of the day. Breakfast is chosen since over-night fasting provides a more stable baseline from which to measure changes due to a meal. Eating the standardized meal first helps to ensure that there is not an impact from food or meals eaten a few hours earlier prior to the standardized meal. In some cases, six or more hours is needed by some individuals to clear fat from their blood. As a result, blood measurement after some other meal, such as dinner may be affected by meals earlier in the day.

As discussed briefly above, the standardized meals may be repeated. Given the high degree of noise inherent in measuring nutritional responses at home, this increases accuracy by having multiple measurements of biomarker responses to the same meals which may be statistically combined to generate a more accurate measure of the individual's response to a particular meal. This may be done using the data accuracy service 120.

To further increase accuracy, meals may be labelled with a barcode (or some other identifier) as well as text such as "Day 1", "Day 2", etc. Prior to consuming the standardized meal, the individual scans the barcode with their computing device 102 which may be a mobile phone. In some examples, an application on the computing device presents a user interface that displays what standardized meal to consume. As an example, the user interface may display "Day 2 Meal". In some instances, the individual is not aware of the nutrients in the standardized meal to help minimize mistakes while ensuring the contents are blinded to the individual. Individuals may also receive notifications through their computing device as reminders. According to some examples, the order of the standardized meals is randomized. This allows adjustment for the impact of the order of previous meals on the reactions to the current one.

In some cases, individuals are allowed to have water, tea or coffee with their standardized meals. According to some examples, an individual can add skimmed milk (no more than 40 ml), no sugar, and is instructed to make the coffee or tea using the same amount each morning and at the same time each morning when testing is performed. The individual can also be instructed to not consume more than one tea or coffee until about four hours after the standardized meal during days when At Home Blood Tests are performed, and until about three hours after the standardized meal on other days.

These standardized meals are designed so that most individuals can consume them all and have enough food that they will be willing to avoid eating anything more for the prescribed period of the measurements after eating. Individuals will be asked to consume the entire amount of food indicated for the standardized meals within a set period of time such as ten minutes and to record any left-over food.

As discussed above, the food data can be determined using different mechanisms. In some examples, food logging can be done via a computing device 102, such as a mobile phone. Outside of the standardized meals in which nutritional responses are measured, individuals are free to eat and drink what they wish during a measurement period, or can choose from a list of recommended foods provided to them. The individuals may be asked to track their meals, snacks and drinks on their mobile device. Individuals are also advised not to change their physical activity patterns during the course of the study. This helps to ensure more accurate results.

To improve data associated with a particular individual, individuals can be provided recommendations to increase the diversity of the food they eat, so as to measure the impact of a wider range of nutritional inputs (e.g. high fiber meals). For example, a recommendation can be provided by the nutritional service based on the foods logged by the application.

According to some examples, the individual logs the food items being eaten, the start time of the meal and the quantity consumed, and the like. To increase the accuracy of the logging, the individual may use the phone's camera to take digital images of the food. In some examples, a photo of the food can be programmatically analyzed to determine the food(s) eaten (See FIG. 3). In some examples, individuals may place an object of a known size, such as a standardized card, with the food being eaten before taking a picture. In this way, the object provides a reference scale for the food being consumed. The purpose of this is to automate recognition of what the food is, and what the quantity is by referencing an object of known scale. To increase the accuracy of the logging, the individual identifies the food from an accurate food database of foods available in that country either by barcode scanning to identify the food or by text-based entry by the user. This database can be stored on the mobile phone and/or at some other location.

By combining user photos with a known item such as a card, with the accurate identity of the food logged by the user from a database and its quantity it is possible to build a large training set of photos of food with accurate labels. One can then utilize an algorithm to automatically estimate the correct food in the photo and its quantity. One can use the photo to automatically capture the start time of the meal, and to provide information to a support team to manually check the accuracy of the user's logging.

By using the computing device 102 to log standardized meals, the start time of consuming the standardized meals can be determined. When the standardized meals have a barcode that is scanned with the phone then it can be determined by the data accuracy service 120 that the correct standardized meal was eaten and that the meal was eaten at the right time. When it is determined that the correct meal was not eaten, the test data can be associated with the actual meal eaten.

According to some examples, some individuals may be asked to visit a clinic to combine at home data with data collected at a clinic. The purpose of the clinic visit is to allow much higher accuracy of measurement for a subset of the individual's data, which can then be combined with the lower-quality at home data. This can be used by the data accuracy service 120 to improve the quality of the at home data.

According to some examples, the day before the visit to the clinic, the individuals are asked to avoid taking part in any strenuous exercise and to limit the intake of alcohol. Individuals are provided with food instructions for the day before to avoid eating high fat or high fiber meals that may interfere with the results the following day. The individuals are asked to fast overnight and instructed to avoid eating or drinking anything except water from the night before their visit. The individuals will be encouraged to drink a lot of water as it will help with cannulation on the day of the visit. They will also be asked to avoid taking any self-prescribed medication on the day of their appointment, but continue taking their doctor-prescribed medicines.

Individuals are instructed to arrive at the clinic in the morning. Following reception and fasting measurements (e.g. blood pressure or heart rate), the individuals are often cannulated. Blood is then taken regularly throughout the visit, so as to accurately capture post-prandial responses. If necessary blood can be centrifuged rapidly and stored in freezers on-site at −80 degrees centigrade, ensuring that clinical assays can be carried out with the highest accuracy of results. This means many metabolites can be measured that could not be measured at home, and that there will be a high degree of accuracy to the results.

At a certain time point when blood is being drawn via cannulation, the individuals will also undergo an "At Home Blood Test" at the clinic, just as if the test were performed at home. The results of this At Home Blood Test can then be correlated with the high-quality measurement done by biological assays on the venous blood, to improve the accuracy of other At Home Blood Test results, both for this individual and any other user of that at home biological collection device. This can also be carried out for at home stool test devices, which may be compared with fresh samples immediately frozen and then assayed.

After a fasting blood draw, the individual consumes a standardized meal, which is consumed within a set time such as ten minutes to ensure consistency of start time across individuals. In the clinical visit this is likely to be a very high fat meal, to allow measurement of triglycerides responses as well as carbohydrates. In some cases, this first meal may be followed by a second meal roughly four hours after the first.

In some cases, this high fat meal may consist of two high fat muffins and a NESQUIK milkshake, or a similar drink. Nutrient profile: 869 kcal, 82 g carb, 55 g fat, 15 g protein, 2 g fiber. When there is a second meal it may consist of a muffin which might contain 600 kcal (75 g Carb, 25 g Fat). This is intended to (1) further differentiate triglycerides responses between individuals in the hours after this meal, and (2) elicit a second insulin & c-peptide response that can be measured during the clinical visit. It will also ensure individuals do not get hungry before the end of the clinical visit.

The clinical visit can also be used to allow trained staff to carry out Anthropometric measures, such as Waist and hip circumference, body weight and body fat composition, height, blood pressure (which can be using an ambulatory blood pressure monitoring device) and heart-rate. This can be compared with at home measurements to identify the accuracy of measurements done by the individuals themselves. In some cases, the individuals can also have a scan such as a DEXA scan to measure further characteristics of the individual such as visceral fat.

The clinical visit can also be used to train individuals on aspects of the at home activities, such as food logging, completing At Home Blood Tests and using their electronic data collection devices, so as to improve compliance and accuracy. In some cases, the electronic data collection devices can be attached at the clinical visit to improve success rates.

There are multiple ways for an individual to carry out an At Home Blood Test to collect their own blood at home without needing a medical professional. Some of these include finger pricks onto dried blood spot cards or other absorbent materials so that the blood dries, finger pricks into collecting vessels so that the sample remains liquid, micro needles or micro filaments into collecting vessels so that the sample remains liquid, as well as other techniques developed or to be developed. Avoiding contamination, accurate timing, conservation of the sample and avoiding misattribution of samples are factors affecting the accuracy of a test. Because at home collection of bodily fluids introduces more noise and error into the measurement, techniques described herein can be utilized to reduce error. In order to improve the accuracy of these tests, more than one test can be combined. For instance, combining the at home blood test results with other measurements such as blood glucose via a CGM may be utilized.

In a clinical visit, blood is taken at multiple occasions usually through a cannula to allow a graph of the post-prandial response of each biomarker to be produced, and the peak and area under curve calculated. This can mean blood is taken at ten different occasions. At home, it is not practical to take blood so many times, for cost reasons and due to compliance since blood-taking at home may involve some discomfort and may be time consuming. In some examples, to measure a post-prandial response at home, at least two blood tests are taken for a single meal. One blood test may occur just before the meal to measure the baseline for the biomarker, and one or more other measurements may be taken after eating the meal. Usually the meal will be at breakfast time, so the first measurement is a fasting measurement. Because only a few time points are taken, it is not possible to accurately plot the whole curve of the biomarker, and if no measurement is taken near the peak of the biomarker's value it is difficult to accurately estimate that peak. Therefore, to be able to use at home measurements of post-prandial responses, care must be taken to determine the optimal time points for the blood taking in order to have useful at home measurements of responses.

Post-prandial measurement are therefore timed to coincide with the peaks for the target biomarkers. For example, measuring around one hour after eating a meal is optimized for peak c-peptide response, and around 4 hours after the meal is optimized for peak triglycerides response. These times can be adjusted based on the particular biomarker being measured. In some examples, the timing of blood tests at home is determined based on measurement of the particular post-prandial response to that meal in a clinical setting to identify the average person's peaks for the target biomarker.

If one wants to capture the post-prandial response of biomarkers which peak rapidly after meals (e.g. c-peptides), and those that peak slowly (e.g. fats such as triglycerides), then this requires at least three time points for blood collection on a single meal. One before the meal (fasting), one measurement at around one hour after the meal, and another measurement at around four hours after the meal. This timing allows peak levels to be captured for a range of biomarkers and then compared between individuals.

The timing of tests performed at home affects how accurate are the results of the test, as many biomarkers change significantly and rapidly post-prandially. The clock used for recording the timing of the tests can be synchronized with the clock used by the CGM, and the clock used for the online food logging before the at home collection begins. This will allow the data to be accurately combined which may be done using the data accuracy service 120. If timing is inaccurate the values measured can be far from their true values. The application 130 operating on the computing device 102 can be programmed to adjust the clocks on the applications running on the device and/or data accuracy service 120 can determine the time differences between each of the clocks such that the data is correlated.

In some examples, to assist in determining these biomarker values, the computing device 102 (e.g., a mobile phone) can be utilized. The individual uses the computing device to record the timing of each At Home Blood Test, providing a timestamp to match to the eventual biological assay results, 109. This helps to identify if the tests are taken at the correct times. If the timing is off, the data accuracy service 120 may adjust the data, reject the data, or use the data with a lower level of weighting when combined with other test data.

In some examples, the computing device 102 (e.g. a mobile phone) provides a user interface 104 that automatically provides notifications to the individual of the correct timing of the At Home Blood Tests, to reduce the likelihood of forgetting to take them.

In some examples, the computing device 102 (e.g. a mobile phone) provides a user interface 104 that for each At Home Blood Test asks an individual to record a picture of the blood sample, to scan a barcode on the sample, and to confirm the time of collection. This helps to ensure that (1) the sample has been taken and the timing of the sample is accurately recorded, (2) the quality of the sample is recorded, (3) if the individual has used the wrong blood collection device (e.g. switched day 2 and day 3, or switched hour 1 and hour 4), this is identified and can be corrected by the data accuracy service 120.

Recording a photo of the samples and delivering it over the Internet, or some other medium, to a qualified support individual can identify issues with the sample quality immediately. If the sample quality is not high, the support individual can identify the issue causing this and speak to the user before the measurement period is finished and teach them how to improve their blood collection process rather than only discover this issue after the user has finished the process and the sample is measured by the biological assays 109.

As discussed above, some of the At Home Blood Tests can involve finger pricks. These have not commonly been used for triglycerides. However, it is possible if clear instructions to avoid contamination are followed. Contamination can be a particular problem, as for example it is the concentration of glycerol in blood that is measured to determine triglyceride concentrations in most commercial assays, and glycerol is common in many hand creams, hair gels, etc. that end up on individual's fingers. To assist in resolving this, each individual is instructed to wash their hands very thoroughly with plenty of soap, then wash all the soap away with clean warm water for at least 30 seconds. Any traces of soap, hand cream, etc. contaminate the results so that they cannot be used. Alcohol wipes should not be used after cleaning the hand.

Blood from finger-pricks is commonly deposited onto paper called Dried Blood Spot cards where it dries. Dried blood spots (DBS) also rely on certain characteristics of the individual such as hematocrit. The error induced by different hematocrit levels is one of the big challenges in using DBS. By measuring DBS in the clinical setting for an individual, and comparing it with venous blood measured using traditional clinical biochemistry, using in clinic biological collection 107 and then biological assays 109, the impact of the individual's hematocrit and other individual characteristics can be calculated and subsequent measurements made in the at home setting can be adjusted for by the data accuracy service 120, increasing accuracy.

To capture relevant information that may affect nutritional responses, the individual can be asked to fill in questionnaires, via computing device 102 which might be a mobile phone. The data from these questionnaires can be used to increase the accuracy of at home measurement by automatically computing likely values for the individual, for example required calories per day which vary by body weight, or certain biomarker responses which may vary depending on sex. The data accuracy service 120 can then compare these with the values measured by devices.

According to some examples, as discussed briefly above, a Continuous Glucose Monitor (CGM) may be attached to the individual for some or all of the period they are being measured at home. This CGM may be attached by the individual themselves at home. The CGM's clock can be synchronized with the clock on the computing device 102, usually by synchronizing both to Internet time. By wearing a CGM it is possible to combine highly accurate glucose data with data captured by other devices. In particular this allows the measurement at home of both the glucose response and one or more other biomarkers to the same meal using an At Home Blood Test. This is beneficial since, for example, many meals that generate low glucose responses are low in carbohydrate but high in fat and it is therefore valuable to measure the fat responses in the blood in order to determine the likely health effects of such a meal rather than rely only on glucose results.

The CGM can also be used to check the timing and content of the meals. If a glucose spike is not triggered shortly after a meal that is known to lead to such spikes (for example most meals that have carbohydrates in them) then this can be used by the data accuracy service 120 to reinterpret the data from an At Home Blood Test, and either reject it or adjust for the correct starting point of the meal. The size of the spike can also help to identify the accuracy of the food logged, so for example if the glucose spike is higher than expected then this could suggest the quantity of food is more than was logged.

As briefly discussed, in some examples qualified individuals can be utilized to provide support to users. When a mobile phone is being used by the user, it is possible to allow such a support team to receive close to real-time information on how the user is behaving. This can be used: (1) To contact the user and improve their food logging, at home blood taking, or other measurement; (2) To quantify the quality of the data coming from the user based on talking to the user (by phone, or via messages). So, for example, if the user says that they struggled to log a particular meal, the data from that meal could be removed while keeping other data; (3) To correctly log food that has not been accurately logged. Because a photo has been taken, the support team can correct the logging of that food. This can be done by speaking to the user directly, or by identifying the food manually, or by building a machine learning algorithm to automatically identify the food. Where food has not been logged accurately, this can be cross-checked with one of the other measurements.

As insulin is not very stable once extracted, it is not a good candidate for at home measurements. To overcome this, this method proposes measuring c-peptide using at home blood tests, and then calculating the insulin level from the value of the c-peptide. This works because c-peptide can be relatively stable over many days, especially if using dried blood tests which are then put in the fridge at home before sending them to be analyzed. To calculate insulin values from c-peptide, it is helpful to have a large benchmark of data from in clinic biological collections 107 comparing the calculated c-peptide levels using the At Home Blood Test process at the clinical visit with the known values of insulin measured very accurately using venous blood and clinical biochemistry at the same time as the At Home Blood Test process. Using this data set it is possible to take one or more c-peptide values from a user's At Home Blood Test(s) and calculate the insulin levels for that individual. This data would be further improved if that individual did a clinical visit to do in clinic biological collections 107 which would provide further data to calculate that individual's relationship between c-peptide and insulin.

The activity level of individuals can be monitored using electronic data collection devices 105 that include devices like accelerometers and heart rate measurement. These can be used to calculate exercise and sleep amongst other things. These can be used as another check by the data accuracy service 120, as for example it isn't possible to be running and doing blood tests at the same time, and it isn't a good baseline blood measurement if the individual has been awake for twelve hours.

To improve the accuracy of at home measurements of nutritional responses, cross-checking can be performed by the data accuracy service 120, the support team, or some other computing device. For example, through cross-checking of various combinations of two or more of: questionnaires, photos taken by the mobile phone, food logged, CGM, At Home Blood Spot recording, Activity level monitoring or other electronic data collection devices, and data recorded by the support team a determination can be made as to whether the data is accurate.

Where there is a conflict between different inputs (e.g. the individual recorded one thing in the app but a wearable device says something different) the data point can be removed from consideration by the data accuracy service 120 or it can reduce its weighting in any machine learning algorithm or other analysis based upon this data.

This cross-checking can be used to determine whether an individual's food logging is missing or the food is not accurately described. For example, this can be identified when there is a glucose spike measured by a CGM without the individual having logged food at that time, or where there is a photo that clearly does not match the food described via the food logging, or where the total calories logged for the day are too little to cover the calculated calorie requirements that come from questionnaire data. It can also be used to identify where an individual's accuracy of food timing is poor, for example where a CGM spike does not closely align with the timing they recorded for their At Home Blood Tests or their food logging. All or a portion of this can be taken into account by the data accuracy service 120.

Figure 2:
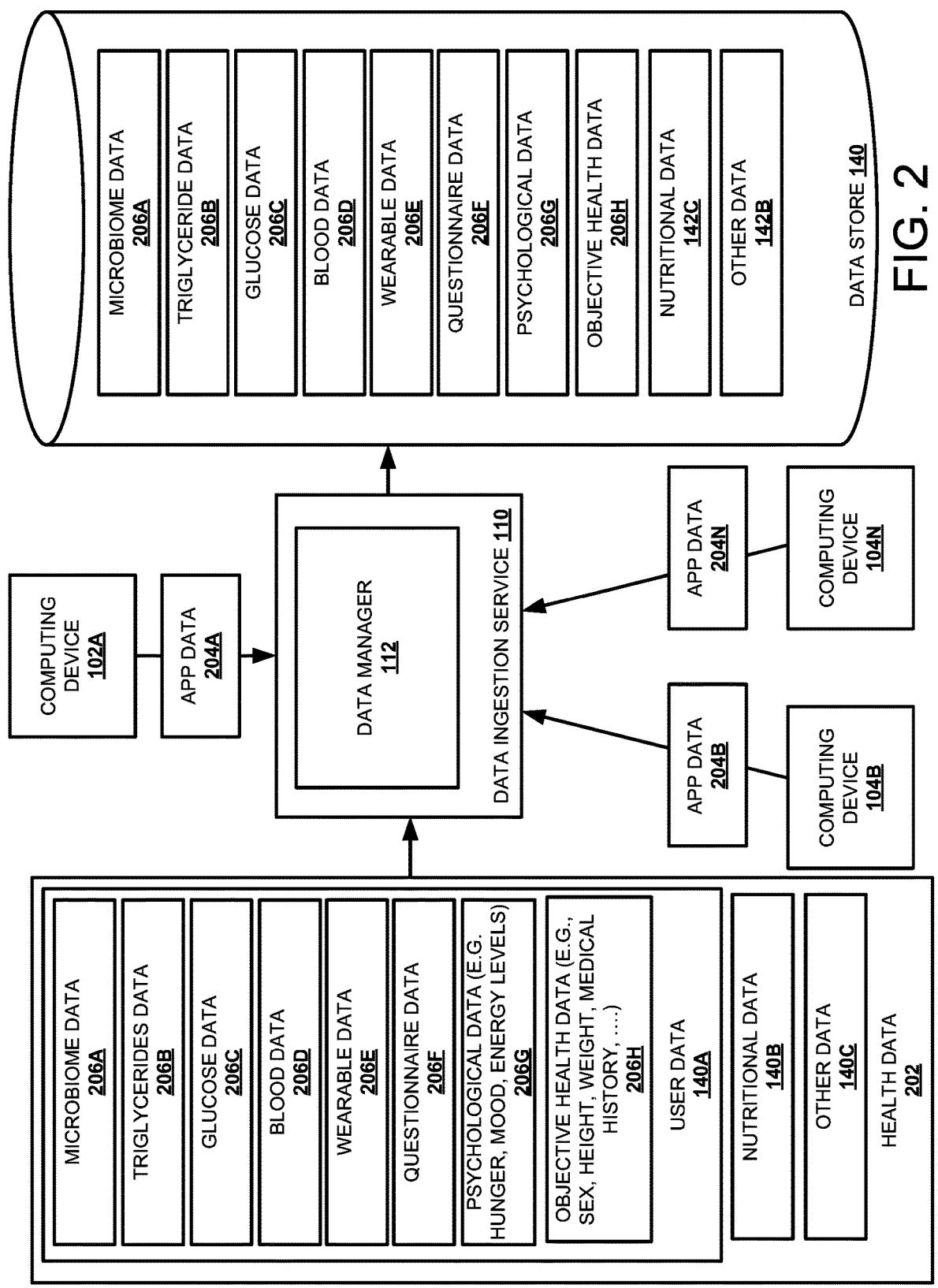
FIG. 2 is a block diagram depicting an illustrative operating environment in which a data ingestion service receives and processes test data associated with at home measurements of nutritional responses.

FIG. 2 is a block diagram depicting an illustrative operating environment 200 in which a data ingestion service 110 receives and processes data associated with test data associated with at home measurements of nutritional responses. As illustrated in FIG. 2, the operating environment 200 includes the data ingestion service 110 that may be utilized in ingesting data utilized by the data accuracy service 120.

In some configurations, the data manager 112 is configured to receive data such as, health data 202 that can include, but is not limited to microbiome data 206A, triglycerides data 206B, glucose data 206C, blood data 206D, wearable data 206E, questionnaire data 206F, psychological data (e.g., hunger, sleep quality, mood, . . . ) 206G, objective health data (e.g., height, weight, medical history, . . . ) 206H, nutritional data 142C, and other data 142B.

According to some examples, the microbiome data 206A includes data about the gut microbiome of an individual. The gut microbiome can host a large number of microbial species (e.g., >1000) that together have millions of genes. Microbial species include bacteria, fungi, parasites, viruses, and archaea. Imbalance of the normal gut microbiome has been linked with gastrointestinal conditions such as inflammatory bowel disease (IBD) and irritable bowel syndrome (IBS), and wider systemic manifestations of disease such as obesity and type 2 diabetes. The microbes of the gut undertake a variety of metabolic functions and are able to produce a variety of vitamins, synthesize essential and nonessential amino acids, and provide other functions. Amongst other functions, the microbiome of an individual provides biochemical pathways for the metabolism of nondigestible carbohydrates; some oligosaccharides that escape digestion; unabsorbed sugars and alcohols from the diet; and host-derived mucins.

The triglycerides data 206B may include data about triglycerides for an individual. In some examples, the triglycerides data 206B can be determined from an At Home Blood Test which in some cases is a finger prick on to a dried blood spot card. The glucose data 206C includes data about blood glucose. The glucose data 206C may be determined from various testing mechanisms, including at home measurements, such as a continuous glucose meter.

The blood data 206D may include blood tests relating to a variety of different biomarkers. As discussed above, at least some blood tests can be performed at home. In some configurations, the blood data 206D is associated with measuring blood sugar, insulin, c-peptides, triglycerides, IL-6 inflammation, ketone bodies, nutrient levels, allergy sensitivities, iron levels, blood count levels, HbA1c, and the like.

The wearable data 206E can include any data received from a computing device associated with an individual. For instance, an individual may wear an electronic data collection device 103, such as an activity-monitoring device, that monitors motion, heart rate, determines how much an individual has slept, the number of calories burned, activities performed, blood pressure, body temperature, and the like. The individual may also wear a continuous glucose meter that monitors blood glucose levels.

The questionnaire data 206F can include data received from one or more questionnaires, and/or surveys received from one or more individuals. The psychological data 206G, that may be subjectively obtained, may include data received from the individual and/or a computing device that generates data or input based on a subjective determination (e.g., the individual states that they are still hungry after a meal, or a device estimates sleep quality based on a movement of the user at night). The objective health data 206H includes data that can be objectively measured, such as but not limited to height, weight, medical history, and the like.

The nutritional data 142C can include data about food. For example, the nutritional data can include nutritional information about different food(s) such as their macronutrients and micronutrients or the bioavailability of its nutrients under different conditions (raw vs cooked, or whole vs ground up). In some examples, the nutritional data 142C can include data about a particular food. For instance, before an individual consumes a particular meal, information about that food can be determined. As briefly discussed, the user might scan a barcode on the food item(s) being consumed and/or take one or more pictures of the food to determine the food, as well as the amount of food, being consumed. In some instances, the user may also take a picture after consuming a meal to determine what food was consumed as well as how much of the food was consumed.

The other data 142B can include other data associated with the individual. For example, the other data 142B can include data that can be received directly from a computer application that logs information for an individual (e.g., food eaten, sleep, . . . ) and/or from the user via a user interface.

In some examples, different computing devices 102 associated with different users provide application data 204 to the data manager 112 for ingestion by the data ingestion service 110. As illustrated, computing device 102A provides app data 204A to the data manager 112, computing device 104B provides app data 204B to the data manager 112, and computing device 104N provides app data 204N to the data manager 112. There may be any number of computing devices utilized.

As discussed briefly above, the data manager 112 receives data from different data sources, processes the data when needed (e.g., cleans up the data for storage in a uniform manner), and stores the data within one or more data stores, such as the data store 140.

The data manager 112 can be configured to perform processing on the data before storing the data in the data store 140. For example, the data manager 112 may receive data for ketone bodies and then use that data to generate ketone body ratios. Similarly, the data manager 112 may process food eaten and generate meal calories, number of carbohydrates, fat to carbohydrate rations, how much fiber consumed during a time period, and the like. The data stored in the data store 140, or some other location, can be utilized by the data accuracy service 120 to determine an accuracy of at home measurements of nutritional responses performed by users.

Figure 3:
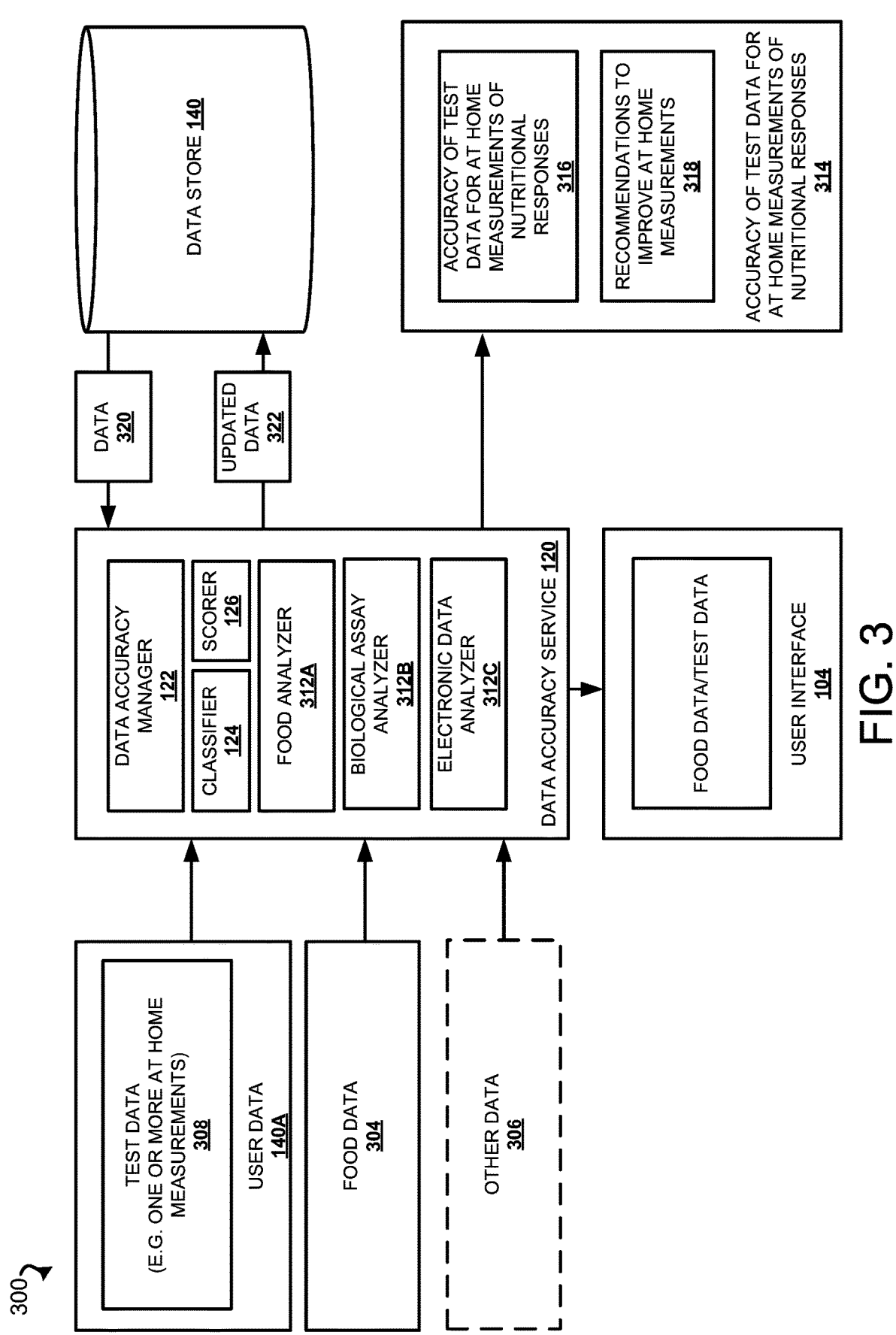
FIG. 3 is a block diagram depicting an illustrative operating environment in which a data accuracy service adjusts test data and/or provides adjustments to at home testing techniques and/or associated with at home measurements of nutritional responses.

FIG. 3 is a block diagram depicting an illustrative operating environment 300 in which a data accuracy service 120 adjusts test data and/or provides adjustments to at home testing techniques that can affect at home measurements of nutritional responses. As illustrated in FIG. 3, the operating environment 300 includes the data accuracy service 120 that includes data accuracy manager 122, classifier 124, scorer 126, food analyzer 312A, biological assay analyzer 312B and electronic data analyzer 312C.

As illustrated, the data accuracy service 120, via the data accuracy manager 122, receives user data 140A including test data 308, food data 304, and optionally other data 306. The accuracy manager 122 utilizes the user data 140A, the food data 304, and possibly other data 306 to analyze and determine the accuracy of test data 308 associated with the at home measurement of one or more biomarkers. In some configurations, the other users' data 140A2 can also be utilized.

As illustrated, the accuracy manager 122 is configured to improve the accuracy of at home measurements of nutritional responses. As discussed above, biomarkers may be measured through one or more at home tests. The tests may include the use of a measuring device, and/or the collection of a bodily fluid (e.g., blood). For example, a portion of the test data can be values of glucose levels, whereas another portion of the test data can be values of insulin levels. As discussed herein, the test data 308 can include data associated with any at home test that measures a nutritional response, and may include some data associated with in clinic collection.

The food data 304 includes data that is associated with the food for which a nutritional response is being measured. The food data 304 can be input by the user either manually and/or automatically. For example, the user may select the food for a particular test from a menu or some other interface. In other examples, the user may scan a barcode of a food item(s) to identify the food associated with the test. In other instances, the user can capture one or more digital images of the food(s). As discussed above, the user may use a camera of a computing device to capture one or more images of the food(s) before the test and, in some examples, one or more images of any remaining food after the user has consumed the food(s).

According to some examples, the food analyzer 312A identifies the food(s) associated with the test(s) by analyzing the food data 304. As discussed above, the food analyzer 312A can identify food based on a barcode associated with the food, and/or identify food that is within a captured image. For example, the food analyzer may use object recognition to identify the food within an image as well as the quantity of food within the image. In some instances, the food analyzer 312A may request input from the user on identifying food that is associated with a test. The other data 306 might include data associated with an activity of the user, information about when the user last ate, and the like. The other data 306 might also include information from other users such as any at home and in clinic test results.

As discussed, the data accuracy service 120 can utilize a machine learning mechanism. The machine learning mechanism can be trained to identify whether test data associated with nutritional tests are accurate. According to some examples, the machine learning mechanism, or some other scoring mechanism weights different data used to determine whether the test data 308 is accurate. For example, some test data 308 associated with a particular measurement for a biomarker may be more accurate than a different test for the same biomarker. Some data may be removed as outside plausible biological ranges or because it is incompatible with other collected data. Further, the machine learning mechanism may use data received from individuals in a structured setting, such as a hospital setting, or a lab setting to assist in determining whether the data is accurate.

According to some examples, the data accuracy manager 122 utilizes the scorer 126 to generate a score (e.g., a numerical value) for a particular test that measures a nutritional response for that user. In other examples, the accuracy manager 122 utilizes the classifier 124 to place the accuracy of the test data into a category (e.g., not accurate, average accuracy, high accuracy) or some other category (e.g., a category based on the value of the score). Generally, the accuracy of a test that measures a nutritional response is related to how closely an individual follows the test protocol for the test being performed. For example, consuming the proper food (including the amount of food), performing the test at the appropriate time(s), and the like.

In some examples, the data accuracy service 120 determines whether data received from an individual performing a test is accurate. For instance, the data accuracy service 120 may determine that an individual incorrectly recorded the time the food was consumed and/or the time the test was taken based on the test data associated with the test (e.g., no glucose response detected after the user indicated a food was eaten that contained carbohydrates). In other examples, the data accuracy service 120 utilizing the biological assay analyzer 312B may detect whether the user correctly filled a bloodspot, and the like. For instance, the biological assay analyzer 312B can detect that not enough blood filled the bloodspot (e.g., by analyzing an image of a bloodspot to determine how much of the bloodspot is filled), that the bloodspot is filled correctly, or that the bloodspot is overfilled. The data accuracy service 120 can also use times recorded by a computing device to determine if the test was performed at the proper time. For instance, the time when an image is captured may be used to determine when the test was started. In other cases, the user might input the time when food was consumed and when the tests were performed. In other examples, the data accuracy service 120 utilizing the electronic data analyzer 312C may detect whether data from an electronic data collection device is accurate, for example if the output of an activity monitor falls within credible ranges for human activity. As discussed above, the data accuracy service 120 can utilize test data 308 as well as other data to determine whether the data match.

In some examples, the data accuracy service 120 utilizes data 320 obtained from the data store 140, or some other data source, when determining the accuracy of test data 308. For instance, the data accuracy service 120 may access test data obtained from clinical settings to determine an accuracy of test data received using an at home measurement. The data accuracy service 120 can also access other data associated with the user such as but not limited to questionnaire data 206F, psychological data 206G, objective health data 206H, and the like.

In some configurations, a computing device 102, such as a mobile phone can be utilized to verify times when tests are performed, food is consumed, what food is consumed, and the like. These times can be used to assist in determining whether or not a test was performed within some predetermined amount of time from ingestion of the food (e.g., at 30 minutes, 1 hour, . . . ). As discussed above, other tests can be used to assist in determining an accuracy of a test. For example, values received from a CGM can be used to determine if the time associated with the ingestion of the food is consistent.

The data accuracy service 120 can update data within the data store 140 based upon the analysis of the accuracy of the test data 308. For example, the data accuracy service 120 may mark any test data that is determined to be inaccurate as not to be used. In other cases, the data accuracy service 120 can update the test data to a different value that is changed as a result of detecting inaccurate data.

The data accuracy service 120 can combine data to improve accuracy, for example by looking at multiple measurements of the same nutritional response. The data accuracy service 120 can correct for systematic error in a test result, for example where it calculates that a particular device such as an At Home Blood Test device consistently over-estimates or under-estimates the correct value for a particular biomarker.

The data accuracy service 120 can also provide recommendations to the user to improve the at home measurements. For example, the data accuracy service 120 may provide the recommendations using user interface 104. As briefly discussed above, the data accuracy service 120 can generate one or more user interfaces, such as a user interface 104, through which an individual, utilizing the computing device 102, or some other computing device, may interact with the data accuracy service 120 and input or view data, such as the test data for nutritional responses or viewing the recommendations to improve the accuracy via the user interface 104.

Figure 4:
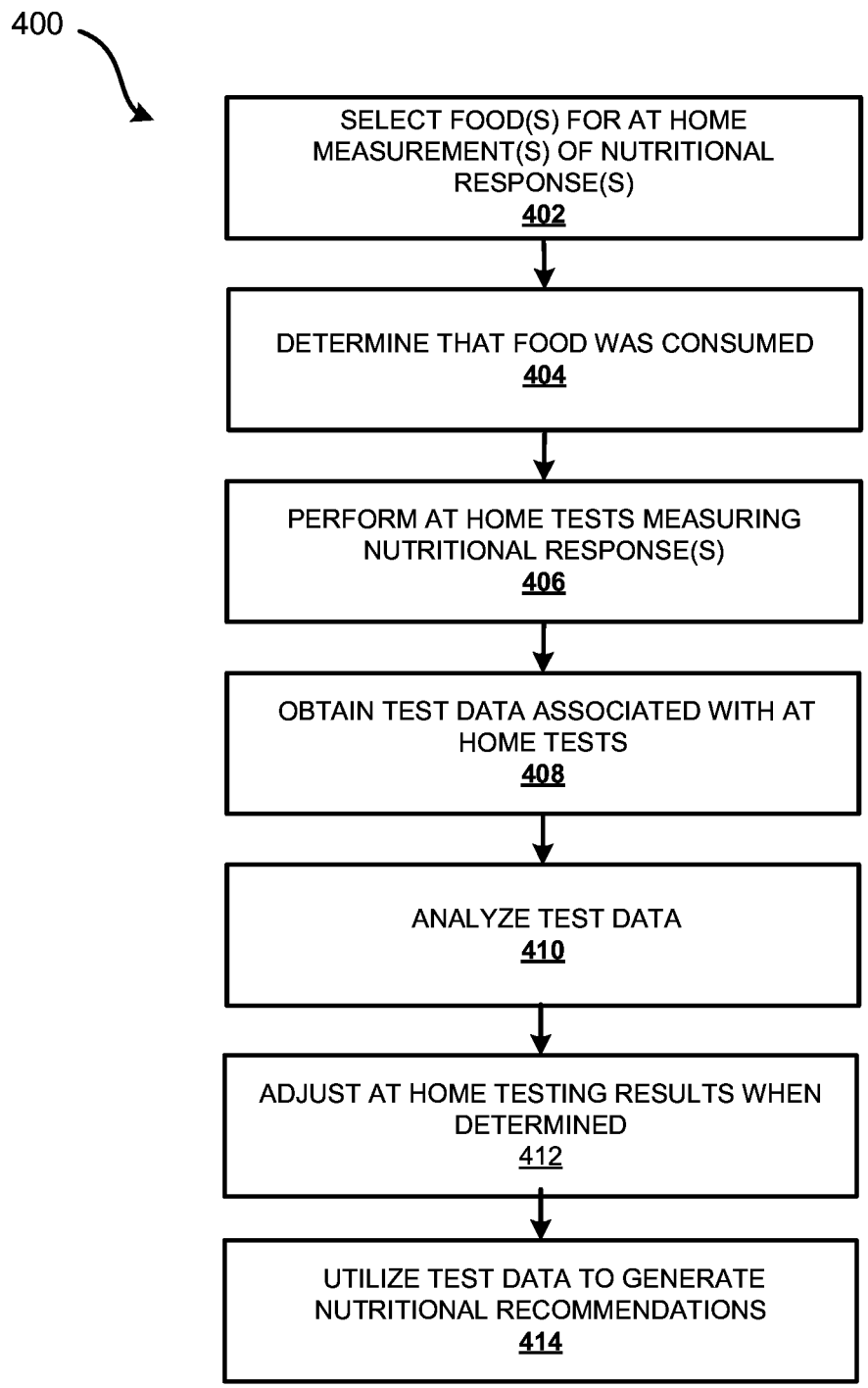
FIG. 4 is a flow diagram showing a routine illustrating aspects of a mechanism disclosed herein for improving the accuracy of at home measurements of nutritional responses.
Figure 5:
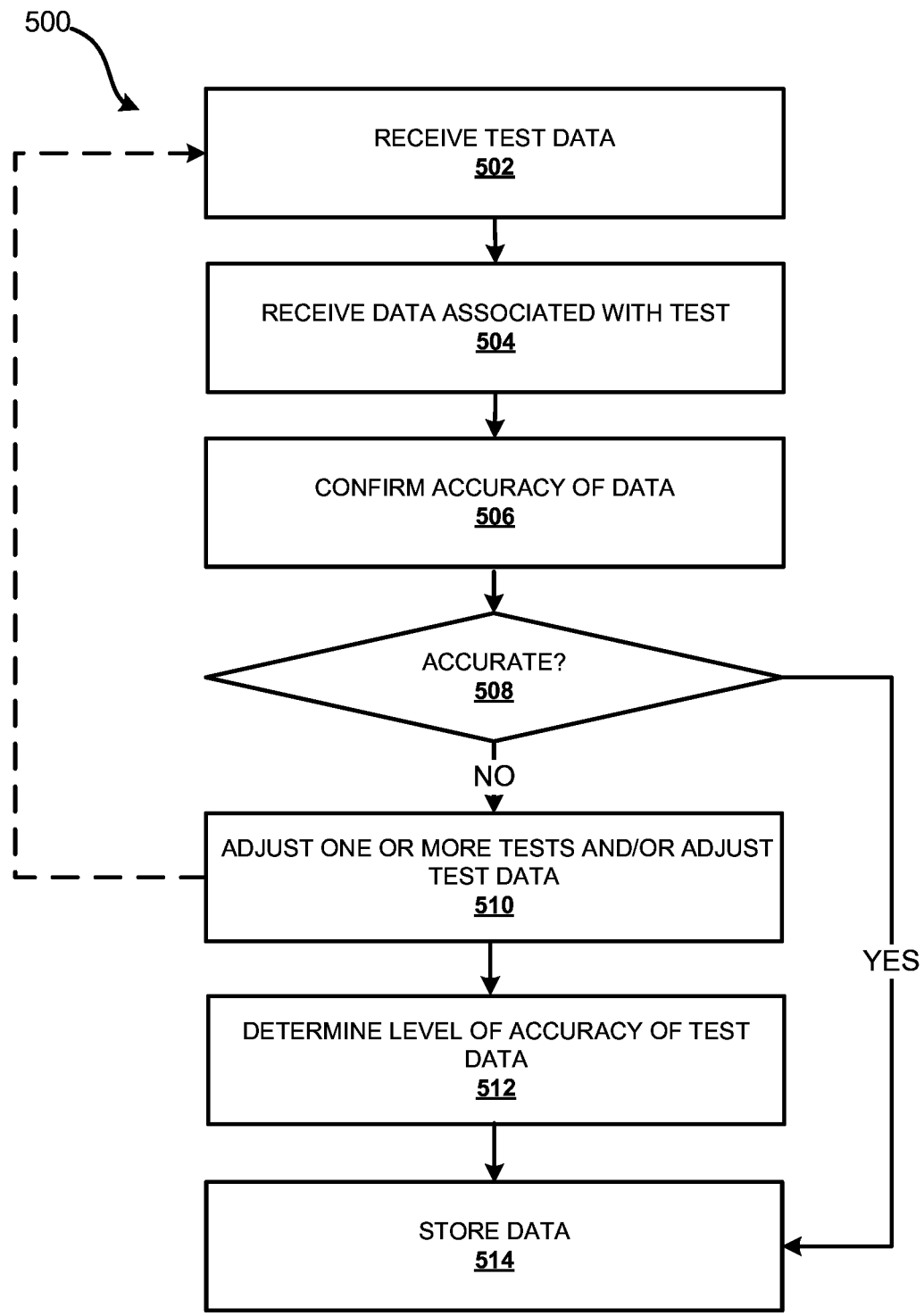
FIG. 5 is a flow diagram showing a routine illustrating aspects of a mechanism disclosed herein for adjusting test data and/or at home testing techniques associated with at home measurements of nutritional responses.

FIGS. 4, and 5 are flow diagrams showing routines 400, and 500, respectively that illustrate aspects of improving the accuracy of measuring nutritional responses in a non-clinical setting in accordance with examples described herein. It should be appreciated that at least some of the logical operations described herein with respect to FIGS. 4, and 5, and the other FIGS., may be implemented (1) as a sequence of computer implemented acts or program modules running on a computing system and/or (2) as interconnected machine logic circuits or circuit modules within the computing system.

The implementation of the various components described herein is a matter of choice dependent on the performance and other requirements of the computing system. Accordingly, the logical operations described herein are referred to variously as operations, structural devices, acts, or modules. These operations, structural devices, acts, and modules may be implemented in software, in firmware, in special purpose digital logic and any combination thereof. It should also be appreciated that more or fewer operations may be performed than shown in the FIGS. and described herein. These operations may also be performed in parallel, or in a different order than those described herein.

FIG. 4 is a flow diagram showing a routine 400 illustrating aspects of a mechanism disclosed herein for improving the accuracy of at home tests to measure nutritional responses. The routine 400 may begin at 402, where food is selected that is consumed to evoke a nutritional response. As discussed above, the food can be a series of standardized meals.

At 404, it is determined that food for a particular standardized meal has been consumed. As discussed above, an individual may log the time the food was consumed. In other examples, the timing may be based on when an image was taken of the food to consume.

At 406, the at home tests measuring one or more nutritional responses are performed. As discussed above, the tests are performed at one or more points in time after eating a particular food, or foods of a meal. As also discussed above, the at home tests can include blood tests, and/or other tests that measure other biomarkers. In some examples, the individual may perform a blood test. In other examples, the individual may perform some other type of test. In some examples, tests are automatically carried out by electronic data collection devices.

At 408, the test data is obtained. As discussed above, the data ingestion service 110 can receive the test data from a computing device 102 or electronic data collection device 103 associated with the individual. In other examples, the test data is received from another source (e.g., the individual returns the collected biological sample via mail or some other courier service and a biological assay 109 is performed that outputs data to the data ingestion service 110).

At 410, the test data is analyzed by the data accuracy service 120. As discussed above, the data accuracy service 120 is configured to determine whether the test data collected by an individual is accurate. For example, was the test data obtained at a proper time as indicated by the test protocol for a particular test?, was the proper test data collected? (e.g., is the bloodspot filled correctly?), was the proper food consumed for the test?, was the proper amount of food consumed?, and the like. As discussed above, the data accuracy service 120 can utilize data received from the computing device 102 (e.g., timing data, image data) to assist in determining whether the test protocol was followed.

At 412, the at home testing results can be adjusted when determined. As discussed above, the data accuracy service 120 may identify that the testing protocol was not followed, and provide instructions to the individual on steps to perform the test properly.

At 414, the test data is utilized. In some examples, the test data is used by a nutritional service to generate nutritional recommendations that are personalized for a particular user. This test data may have been adjusted by the data accuracy service 120. This test data may have been provided with a weight by the data accuracy service which is taken into account by the nutritional recommendation service, which in some cases may involve machine learning mechanisms.

FIG. 5 is a flow diagram showing a routine 500 illustrating aspects of a mechanism disclosed herein for improving the accuracy of at home tests to measure nutritional responses. The routine 500 may begin at 502, where test data is received. As discussed above, the test data can include measurements obtained by a measuring device (e.g., a CGM), a measurement input by an individual, one or more images, and the like.

At 504, data associated with the test is obtained. As discussed above, the data accuracy service 120 may obtain data from a mobile computing device associated with an individual performing the test. The data can include timing data (e.g., when was the food consumed, when was the test performed), data showing pictures of the food and/or results of collection of a sample (e.g., a digital image of a picture of a blood spot), and the like.

At 506, the data accuracy service 120 determines whether the test data is accurate. As discussed above, the accuracy manager 122 of the data accuracy service 120 can utilize a machine learning mechanism to determine whether the data is accurate.

At 508, a determination is made as to whether the test data is accurate. When the test data is not accurate, the process flows to 510. When the test data is accurate, the process moves to 514.

At 510, adjustments are made to one or more tests and/or at least a portion of the test data is adjusted. According to some configurations, the data accuracy service 120 can generate recommendations that are provided to the individual performing the tests. For instance, the data accuracy service 120 may provide information, via a user interface, that instructs the user on how to perform a test. As an example, the data accuracy service 120 may provide an image of a properly collected blood spot and inform the user on why the last blood spot collected was not correctly obtained (e.g., too much blood, not enough blood). In other examples, the data accuracy service 120 may adjust one or more values after determining that the test was performed at a different time than indicated.

At 512, the level of accuracy of the test data is determined. As discussed above, the data accuracy service 120 is configured to determine the level of accuracy of the data At 514, the test data and its level of accuracy is stored. As discussed above, the data accuracy service 120 can store the test data in the data store 140.

Figure 6:
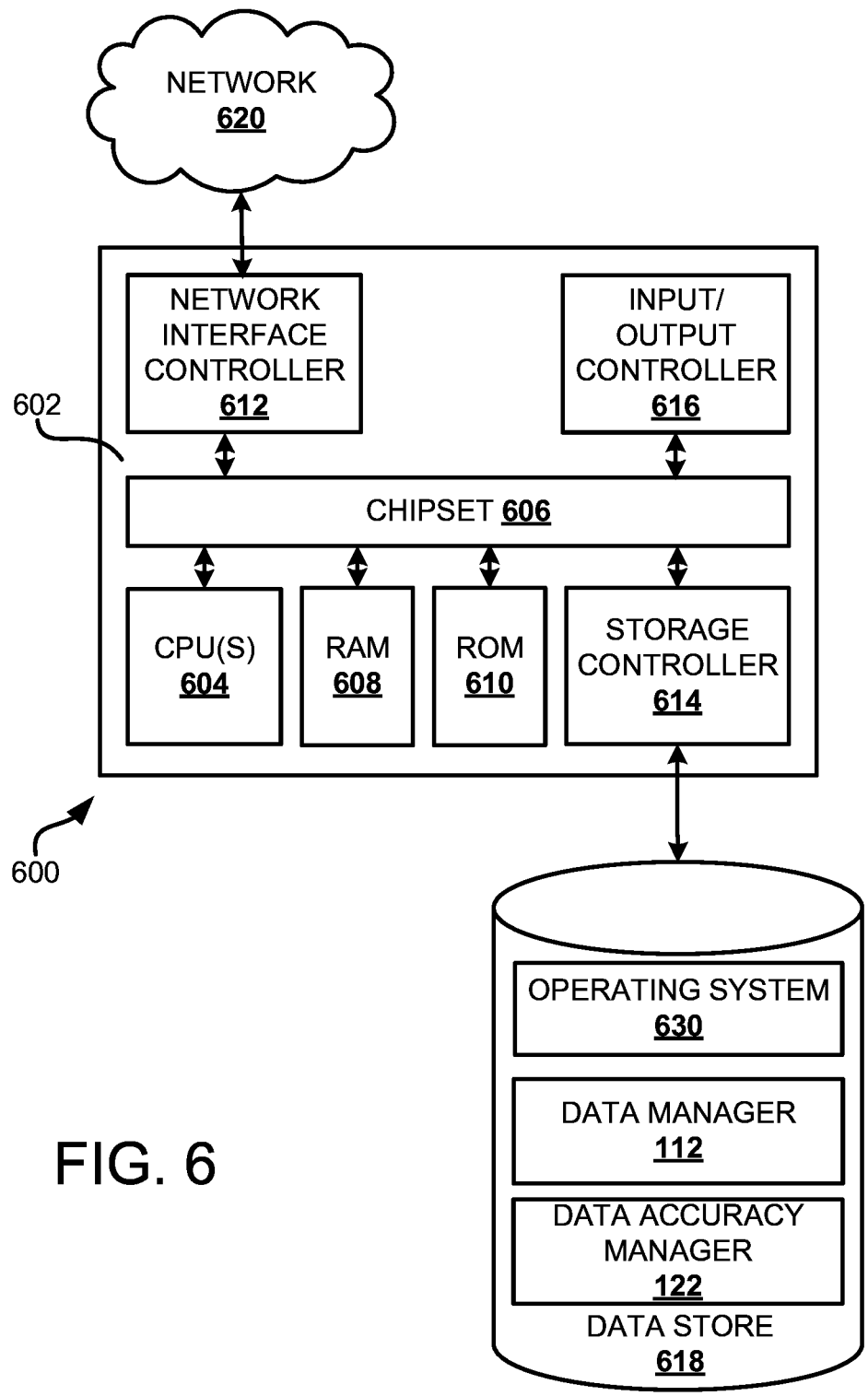
FIG. 6 is a computer architecture diagram showing one illustrative computer hardware architecture for implementing a computing device that might be utilized to implement aspects of the various examples presented herein.

FIG. 6 shows an example computer architecture for a computer 600 capable of executing program components for improving the accuracy of measuring nutritional responses in a non-clinical setting in the manner described above. The computer architecture shown in FIG. 6 illustrates a conventional server computer, workstation, desktop computer, laptop, tablet, network appliance, digital cellular phone, smart watch, or other computing device, and may be utilized to execute any of the software components presented herein. For example, the computer architecture shown in FIG. 6 may be utilized to execute software components for performing operations as described above. The computer architecture shown in FIG. 6 might also be utilized to implement a computing device 102, or any other of the computing systems described herein.

The computer 600 includes a baseboard 602, or "motherboard," which is a printed circuit board to which a multitude of components or devices may be connected by way of a system bus or other electrical communication paths. In one illustrative example, one or more central processing units ("CPUs") 604 operate in conjunction with a chipset 606. The CPUs 604 may be standard programmable processors that perform arithmetic and logical operations necessary for the operation of the computer 600.

The CPUs 604 perform operations by transitioning from one discrete, physical state to the next through the manipulation of switching elements that differentiate between and change these states. Switching elements may generally include electronic circuits that maintain one of two binary states, such as flip-flops and electronic circuits that provide an output state based on the logical combination of the states of one or more other switching elements, such as logic gates. These basic switching elements may be combined to create more complex logic circuits, including registers, adders-subtractors, arithmetic logic units, floating-point units and the like.

The chipset 606 provides an interface between the CPUs 604 and the remainder of the components and devices on the baseboard 602. The chipset 606 may provide an interface to a RAM 608, used as the main memory in the computer 600. The chipset 606 may further provide an interface to a computer-readable storage medium such as a read-only memory ("ROM") 610 or non-volatile RAM ("NVRAM") for storing basic routines that help to startup the computer 600 and to transfer information between the various components and devices. The ROM 610 or NVRAM may also store other software components necessary for the operation of the computer 600 in accordance with the examples described herein.

The computer 600 may operate in a networked environment using logical connections to remote computing devices and computer systems through a network, such as the network 620. The chipset 606 may include functionality for providing network connectivity through a network interface controller ("NIC") 612, such as a mobile cellular network adapter, WiFi network adapter or gigabit Ethernet adapter. The NIC 612 is capable of connecting the computer 600 to other computing devices over the network 620. It should be appreciated that multiple NICs 612 may be present in the computer 600, connecting the computer to other types of networks and remote computer systems.

The computer 600 may be connected to a mass storage device 618 that provides non-volatile storage for the computer. The mass storage device 618 may store system programs, application programs, other program modules and data, which have been described in greater detail herein. The mass storage device 618 may be connected to the computer 600 through a storage controller 614 connected to the chipset 606. The mass storage device 618 may consist of one or more physical storage units. The storage controller 614 may interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 600 may store data on the mass storage device 618 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 618 is characterized as primary or secondary storage and the like.

For example, the computer 600 may store information to the mass storage device 618 by issuing instructions through the storage controller 614 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 600 may further read information from the mass storage device 618 by detecting the physical states or characteristics of one or more particular locations within the physical storage units.

In addition to the mass storage device 618 described above, the computer 600 may have access to other computer-readable storage media to store and retrieve information, such as program modules, data structures, or other data. It should be appreciated by those skilled in the art that computer-readable storage media is any available media that provides for the non-transitory storage of data and that may be accessed by the computer 600.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 618 may store an operating system 630 utilized to control the operation of the computer 600. According to one example, the operating system comprises the LINUX operating system. According to another example, the operating system comprises the WINDOWS® SERVER operating system from MICROSOFT Corporation. According to another example, the operating system comprises the iOS operating system from Apple. According to another example, the operating system comprises the Android operating system from Google or its ecosystem partners. According to further examples, the operating system may comprise the UNIX operating system. It should be appreciated that other operating systems may also be utilized. The mass storage device 618 may store other system or application programs and data utilized by the computer 600, such as components that include the data manager 122, the data accuracy manager 132 and/or any of the other software components and data described above. The mass storage device 618 might also store other programs and data not specifically identified herein.

In one example, the mass storage device 618 or other computer-readable storage media is encoded with computer-executable instructions that, when loaded into the computer 600, create a special-purpose computer capable of implementing the examples described herein. These computer-executable instructions transform the computer 600 by specifying how the CPUs 604 transition between states, as described above. According to one example, the computer 600 has access to computer-readable storage media storing computer-executable instructions which, when executed by the computer 600, perform the various routines described above with regard to FIGS. 3-5. The computer 600 might also include computer-readable storage media for performing any of the other computer-implemented operations described herein.

The computer 600 may also include one or more input/output controllers 616 for receiving and processing input from a number of input devices, such as a keyboard, a mouse, a touchpad, a touch screen, an electronic stylus, or other type of input device. Similarly, the input/output controller 616 may provide output to a display, such as a computer monitor, a flat-panel display, a digital projector, a printer, a plotter, or other type of output device. It will be appreciated that the computer 600 may not include all of the components shown in FIG. 6, may include other components that are not explicitly shown in FIG. 6, or may utilize an architecture completely different than that shown in FIG. 6.

Based on the foregoing, it should be appreciated that technologies for improving the accuracy of the measurement of nutritional responses in a non-clinical setting have been presented herein. Moreover, although some of the subject matter presented herein has been described in language specific to computer structural features, methodological acts and computer readable media, it is to be understood that the invention defined in the appended claims is not necessarily limited to the specific features, acts, or media described herein. Rather, the specific features, acts and media are disclosed as example forms of implementing at least some of the claims.

The subject matter described above is provided by way of illustration only and should not be construed as limiting. Furthermore, the claimed subject matter is not limited to implementations that solve any or all disadvantages noted in any part of this disclosure. Various modifications and changes may be made to the subject matter described herein without following the examples and applications illustrated and described, and without departing from the true spirit and scope of the present invention, which is set forth in the following claims.

What is claimed is:

1. A method, comprising:
generating, by one or more computing devices, a weighting of data to be used by a machine learning mechanism to be used to make predictions of an accuracy of a type of test performed in one or more non-clinical settings based, at least in part, on at least one of clinical measurements of nutritional responses or at home measurements of nutritional responses;

receiving food data, wherein the food data indicates one or more foods consumed by an individual to evoke a nutritional response associated with a test performed in a non-clinical setting;

receiving test data associated with performance of the test in the non-clinical setting;

causing the machine learning mechanism, that uses the weighting, to execute on a computing device or at least one or more of the computing devices, wherein executing the machine learning mechanism includes performing actions to determine an accuracy of the test; wherein determining the accuracy of the test is based at least in part on two or more of the food data, the test data, second test data, or non-biomarker test data, wherein the accuracy of the test is related to how closely an individual follows a test protocol for the test; and causing, based at least on the determined accuracy of the test, at least one of the following to be performed:
confirming the test data by verifying at least a time when one or more foods are consumed based at least in part on a measurement of a blood sugar change received from a continuous glucose monitor (CGM);
confirming the test data by verifying at least a digital image of an At Home Blood Test;
calculating the value of a second biomarker from biomarker data associated with a first biomarker, wherein the first biomarker and the second biomarker are different biomarkers;
combining the value of two or more different biomarker measurements to increase the accuracy of the test;
adjusting at least a portion of the test data at least partly in response to determining that the test was performed at a different time than an indicated time based at least in part on a measurement of a blood sugar change received from the CGM; or
adjusting a weighting of one or more of the food data or the test data when utilized in combination with other data to train or make predictions by a subsequent machine learning mechanism, wherein the weighting reflects an accuracy of the one or more of the food data or the test data versus the accuracy of the other data.

2. The method of claim 1, further comprising receiving the second test data associated with a performance of a second test in the non-clinical setting.

3. The method of claim 2, wherein the test data and the second test data are recorded by both the CGM and by an At Home Blood Test respectively that measure different biomarker responses to a same food.

4. The method of claim 1, further comprising receiving timing data from a computing device associated with the individual, and wherein determining the accuracy of the test is based, at least in part, on the timing information.

5. The method of claim 1, wherein receiving the test data includes receiving the digital image of an At Home Blood Test and wherein determining the accuracy includes determining that the At Home Blood Test was properly performed and/or at which time and/or using which device.

6. The method of claim 1, wherein the test includes a measurement of a blood sugar change by the CGM, and wherein the measurement is used to verify a recorded time associated with consuming the food.

7. The method of claim 1, further comprising utilizing c-peptide measurements in at home blood tests to model insulin post-prandial responses.

8. The method of claim 7, wherein the model incorporates data collected in a clinical setting.

9. The method of claim 1, wherein the test data is collected with an At Home Blood Test, and wherein the second test data is collected with At Home Blood Test(s) where the individual consumes a same at home standardized meal.

10. The method of claim 1, wherein the test data is collected with an At Home Blood Test and the second test data is collected with At Home Blood Test(s) where the individual consumes at home standardized meals of different compositions.

11. The method of claim 1, where the non-biomarker test data includes at least one of questionnaire data, data recorded by the support team, or activity monitoring device data, and wherein determining the accuracy includes cross-checking the non-biomarker test data against one or more of the food data or the test data.

12. The method of claim 1, wherein the second test data is collected from the individual in a clinical setting.

13. The method of claim 1, wherein the food data incorporates food photographs which include an object of known size, and wherein the photographs are processed with automated recognition of the food and quantity of the food.

14. The method of claim 1, further comprising training the machine learning mechanism using a training data set, wherein the training data set is associated with test data from a plurality of individuals for measured biomarker responses associated with eating one or more food items.

15. The method of claim 1, wherein the test data includes data associated with a microbiome test.

16. The method of claim 1, wherein the test data includes data associated with an At Home Blood Test.

17. A system, comprising:
a data ingestion service, including one or more processors, configured to:
receive test data associated with performance of a test by an individual in a non-clinical setting, wherein the test measures a nutritional response; and
receive food data, wherein the food data indicates one or more foods consumed by the individual to evoke the nutritional response associated with the test performed in a non-clinical setting; and
a data accuracy service, including one or more processors, configured to:
generate, by the one or more processors or one or more other computers, a weighting of data to be used by a machine learning mechanism to be used to make predictions of the accuracy of a type of test performed in one or more non-clinical settings based, at least in part, on at least one of clinical measurements of nutritional responses or at home measurements of nutritional responses;
cause the machine learning mechanism, that uses the weighting, to execute on by the one or more processors or the one or more other computers, wherein executing the machine learning mechanism includes performing actions to determine an accuracy of the test wherein determining the accuracy of the test is based at least in part on two or more of the food data, the test data, second test data, or non-biomarker test data, wherein the accuracy of the test is related to how closely an individual follows a test protocol for the test; and
causing, based at least on the determined accuracy of the test, at least one of the following to be performed:

confirming the test data by verifying at least a time when one or more foods are consumed based at least in part on a measurement of a blood sugar change received from a continuous glucose monitor (CGM);

confirming the test data by verifying at least a digital image of an At Home Blood Test;

calculating the value of a second biomarker from biomarker data associated with a first biomarker, wherein the first biomarker and the second biomarker are different biomarkers;

combining the value of two or more different biomarker measurements to increase the accuracy of the test;

adjusting at least a portion of the test data at least partly in response to determining that the test was performed at a different time than an indicated time based at least in part on a measurement of a blood sugar change received from the CGM; or adjusting a weighting of one or more of the food data or the test data when utilized in combination with other data to train or make predictions by a subsequent machine learning mechanism, wherein the weighting reflects an accuracy of the one or more of the food data or the test data versus the accuracy of the other data.

18. The system of claim 17, wherein the test data and the second test data are recorded by a CGM and by an At Home Blood Test that measure different biomarker responses to a same food.

19. The system of claim 17, wherein the test data includes data for a digital image of a blood spot, a scan of a barcode, or a QR code on a blood spot card and wherein determining the accuracy includes determining that the blood spot is properly obtained.

20. The system of claim 17, wherein the test data includes data associated with an At Home Blood Test.

* * * * *